(12) United States Patent
Nuxoll et al.

(10) Patent No.: US 12,138,369 B2
(45) Date of Patent: Nov. 12, 2024

(54) MAGNETICALLY-ACTIVATED COATING FOR TREATING BIOFILMS, AND ASSOCIATED SYSTEMS AND METHODS

(71) Applicant: University of Iowa Research Foundation, Iowa City, IA (US)

(72) Inventors: Eric Nuxoll, Iowa City, IA (US); Joel Coffel, Iowa City, IA (US); Erica Ricker, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 174 days.

(21) Appl. No.: 16/312,680

(22) PCT Filed: Jun. 27, 2017

(86) PCT No.: PCT/US2017/039566
§ 371 (c)(1),
(2) Date: Dec. 21, 2018

(87) PCT Pub. No.: WO2018/005541
PCT Pub. Date: Jan. 4, 2018

(65) Prior Publication Data
US 2019/0209743 A1     Jul. 11, 2019

Related U.S. Application Data

(60) Provisional application No. 62/355,100, filed on Jun. 27, 2016.

(51) Int. Cl.
*A61L 31/14*      (2006.01)
*A61B 18/04*      (2006.01)
(Continued)

(52) U.S. Cl.
CPC .............. *A61L 31/14* (2013.01); *A61B 18/04* (2013.01); *A61F 2/0077* (2013.01); *A61F 7/00* (2013.01);
(Continued)

(58) Field of Classification Search
CPC ....................................................... A61B 18/04
See application file for complete search history.

(56) References Cited

U.S. PATENT DOCUMENTS 6,475,434 B1   11/2002  Darouiche
7,025,778 B2    4/2006  Hayashi et al.
(Continued)

FOREIGN PATENT DOCUMENTS

CA          2697012 A1      1/2009
WO   WO-2013022201 A1 *   2/2013   ........... A61K 31/395

OTHER PUBLICATIONS

Definition of "zone". Merriam-Webster Dictionary. Accessed online on Feb. 2, 2022 at https://www.merriam-webster.com. (Year: 2022).*
(Continued)

*Primary Examiner* — Carlos A Azpuru
*Assistant Examiner* — Casey S Hagopian
(74) *Attorney, Agent, or Firm* — Dentons Davis Brown; Matthew Coryell

(57) ABSTRACT

A system for disrupting a biofilm on a medical device that comprises an implantable medical device; a magnetically-sensitive coating on the surface of the implantable device comprising a polymer and magnetic particles embedded within the polymer; and a coil element capable of generating an alternating magnetic field, wherein the coil element is constructed and arranged to be capable of applying an alternating magnetic field to induce heating of the surface of the implantable device.

8 Claims, 29 Drawing Sheets

(51) Int. Cl.

| | |
|---|---|
| *A61F 2/00* | (2006.01) |
| *A61F 7/00* | (2006.01) |
| *A61F 7/12* | (2006.01) |
| *A61L 2/00* | (2006.01) |
| *A61L 27/34* | (2006.01) |
| *A61L 27/50* | (2006.01) |
| *A61L 29/08* | (2006.01) |
| *A61L 29/14* | (2006.01) |
| *A61L 31/10* | (2006.01) |
| *A61N 2/00* | (2006.01) |
| *A61N 2/02* | (2006.01) |

(52) U.S. Cl.
CPC ............... *A61F 7/12* (2013.01); *A61F 7/123* (2013.01); *A61L 2/00* (2013.01); *A61L 27/34* (2013.01); *A61L 27/50* (2013.01); *A61L 29/085* (2013.01); *A61L 29/14* (2013.01); *A61L 31/10* (2013.01); *A61N 2/02* (2013.01); *A61F 2007/126* (2013.01); *A61F 2210/009* (2013.01); *A61L 2400/18* (2013.01); *A61L 2420/06* (2013.01); *A61N 2/002* (2013.01)

(56) References Cited

U.S. PATENT DOCUMENTS

| | | | |
|---|---|---|---|
| 8,048,471 | B2 | 11/2011 | Nesbitt |
| 8,182,859 | B2 | 5/2012 | Atanasoska et al. |
| 2002/0066702 | A1 | 6/2002 | Liu |
| 2004/0030379 | A1* | 2/2004 | Hamm ................. A61K 31/335 623/1.34 |
| 2009/0263455 | A1* | 10/2009 | Zanella ................ A61K 9/0024 424/426 |

OTHER PUBLICATIONS

Coffel et al., "Controlled, Wireless Heating of Iron Oxide Nanoparticle Composites", AIChE Annual Meeting, Nov. 2014. (Year: 2014 ).*

Coffel, Joel, et al., "Magnetic nanoparticle/polymer composites for medical implant infection control", Journals of Materials Chemistry, vol. 3, pp. 7538-7545, Aug. 25, 2015.

* cited by examiner

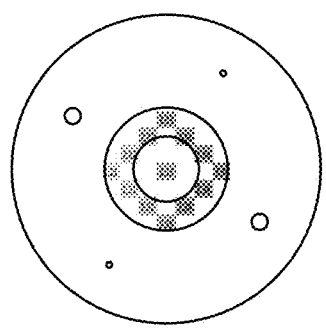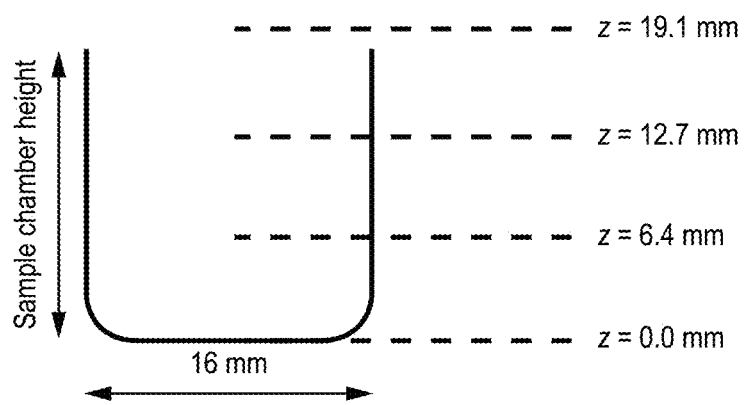
FIG. 4A
FIG. 4B
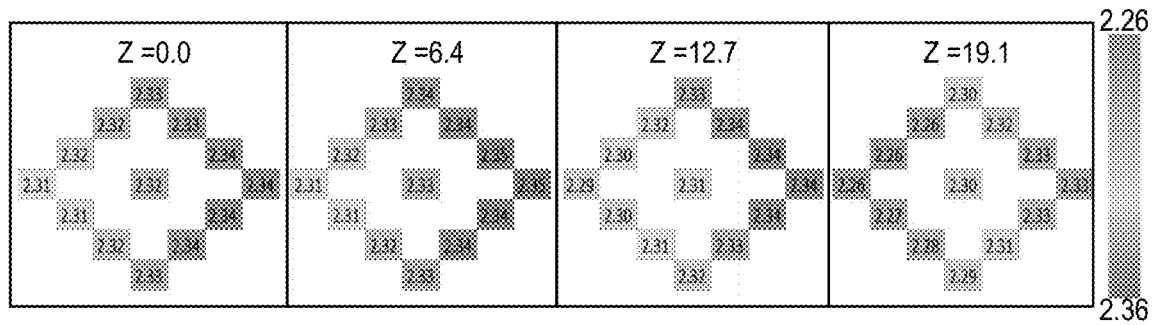
FIG. 4C  FIG. 4D  FIG. 4E  FIG. 4F

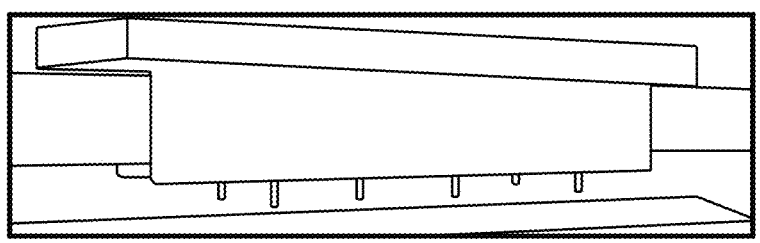
FIG. 7A
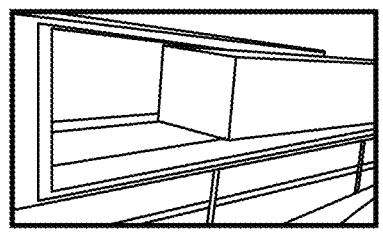 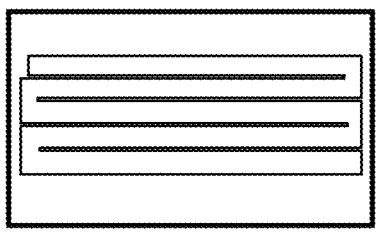
FIG. 7B            FIG. 7C

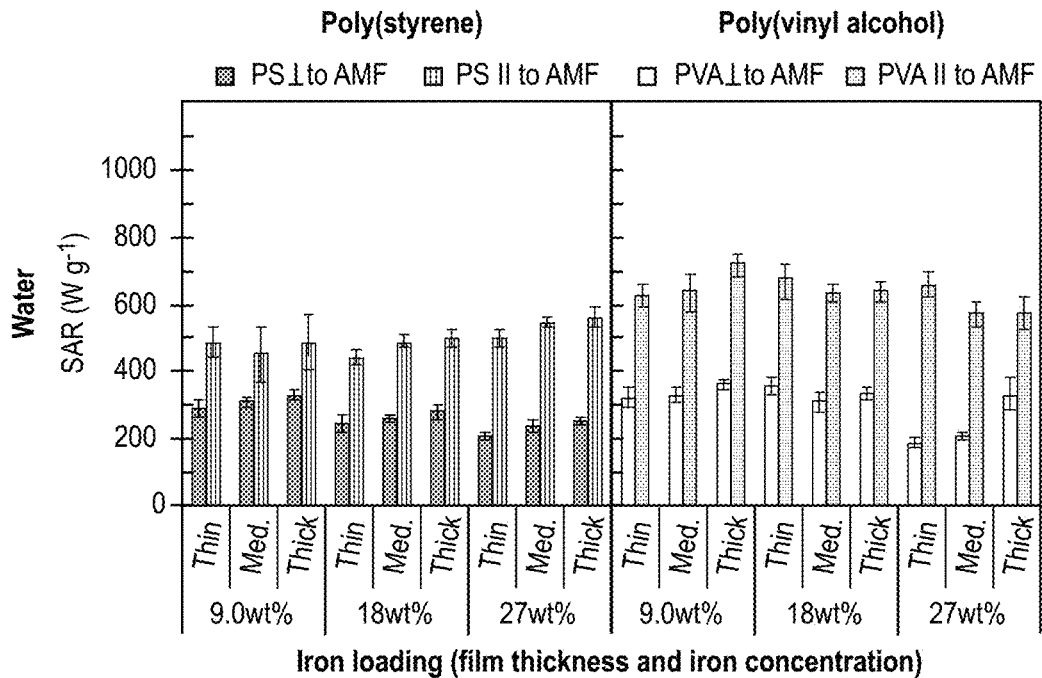
FIG. 9A  FIG. 9B
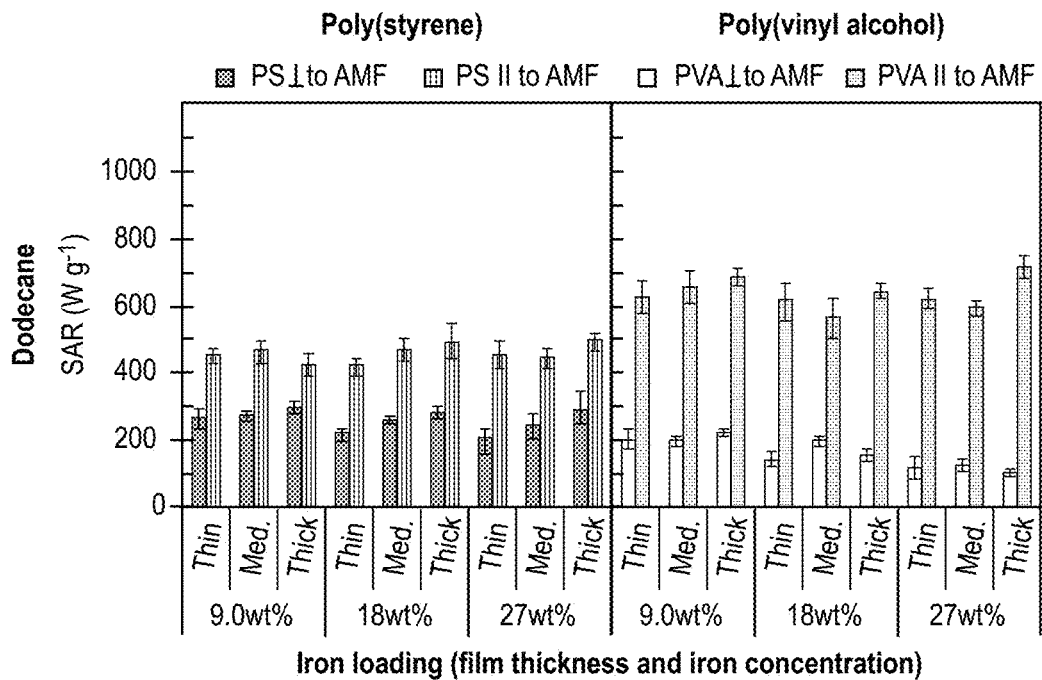
FIG. 9C  FIG. 9D

Control

Heat-Shocked

MAGNETICALLY-ACTIVATED COATING FOR TREATING BIOFILMS, AND ASSOCIATED SYSTEMS AND METHODS

CROSS-REFERENCE TO RELATED APPLICATION(S)

This Application claims the benefit of U.S. Provisional Application No. 62/355,100, filed on Jun. 27, 2016; which is incorporated herein by reference in its entirety.

GOVERNMENT SUPPORT

This invention was made with government support under GM008365 awarded by the National Institutes of Health and CBET1133297 awarded by the National Science Foundation. The government has certain rights in the invention.

TECHNICAL FIELD

The disclosed technology relates generally to the treatment and prevention of biofilms, and in particular, to the devices, methods, and design principles for magnetically-induced thermal-shocks of biofilms by way of a magnetically-sensitive coating. This has implications for implanted medical devices, such as replacement joints.

This disclosure discusses both the process for killing the biofilm and a coating which will supply the heat if the device surface itself is not already magnetically susceptible. This invention can eliminate the multiple surgeries and prolonged hospital stays required for the treatment of infected medical implants, the financial costs of which are several billion dollars per year in the United States alone.

BACKGROUND

The disclosure relates to apparatus, systems and methods for the reduction of biofilms. Roughly 45% of all nosocomial, or hospital acquired, infections are device related. Over 100,000 of the 3.6 million medical devices implanted in the United States each year develop a nosocomial infection, typically manifesting as a biofilm on the device surface. These biofilms can lead to systemic infections causing the mortality of otherwise relatively healthy patients. Of the total episodes of systemic infections 51.4% are nosocomial with crude mortalities ranging from 20 to 40% depending on the pathogen. The most common treatment for these implant infections is high doses of antibiotics and removal of the implant until the infection subsides. Once the patient is clear of infection a third surgery may be performed to place a new implant, though the infection risk is higher for the replacement device. Incidence of nosocomial prosthetic joint infections increase from 1.5-2.5% upon initial surgery to 3.2-5.6% in revision surgeries demonstrating that additional surgeries increase the risk of having an infection. In addition to the long recovery time and decreased quality of life, these biofilm infections are expensive with an estimated cost of $6 billion annually in the United States alone.

Biofilms are formed when planktonic, or free swimming, bacteria adhere to a surface and begin to form an extracellular polymeric substance (EPS). The EPS is comprised of glycolipids, glycoproteins, polysaccharides, proteins, and DNA. The bacteria can replicate and disperse with time and possibly cause a life threatening systemic infection in the patient. One reason for the increasing interest in biofilms is their inherently heightened resistance to antibiotics. Both antibiotics and the host's immune system are less effective against biofilms than they are against planktonic bacteria. While planktonic bacteria typically show inhibition at antibiotic concentrations well below 128 mg/L, biofilms have been shown to require antibiotic concentrations up to 128 times higher than their planktonic counterparts. However, such high antibiotic doses lead to host cell toxicity long before eradication of the biofilm can occur. This increased resistance to antimicrobial application in biofilms is due to the protection provided by the EPS, the limited transport through the EPS, changes in gene regulation, and the presence of persistor cells. On fully implanted devices, these biofilms are also physically inaccessible, prompting explanation surgery in order to remove the biofilm, followed by re-implantation surgery once the infection has cleared.

Many approaches to preventing biofilm formation on medical implants have been investigated; most fall into one of three main categories: drug-eluting surfaces, antimicrobial surfaces, and antiadhesion surfaces. Drug elution is in practice clinically for joint implants, but often results in an increase in the bacteria's antibiotic resistance since the antibiotics often elute late and in lower amounts than the minimum inhibitory concentration. Moreover, multiple antibiotics would be needed to address the full spectrum of possible pathogens. Similarly, antimicrobials immobilized to the implant surface would also need to be broad spectrum and would therefore lack some of the antimicrobial specialization needed to mitigate all possible pathogenic complications. The greater challenge to this approach, however, is surface fouling by non-specific proteins simply covering the antimicrobial agents. Many surfaces that result in lower bacterial adhesion to the implant also decrease the implant's capability to integrate well with the patient's body, prolonging recovery.

Once a biofilm has formed on an implant it becomes more difficult to eradicate the bacteria. There are many strategies being researched such as using DC-current to dislodge the bacteria from the implant. This has shown to be successful in removing bacteria from bone pins in a goat model however, it requires either a large on-board power supply and telemetry or protruding external connections, both of which are undesirable for implanted devices. Another approach uses particles or ions such as silver to break up the EPS, exposing the bacteria to the host's immune system and antibiotics. While growing in popularity, the high concentrations required by this method can cause cytotoxicity to the host cells, preventing advancement to a clinical setting. Enzymes are also being used to target EPS and in combination therapies with antibiotics, showing great potential though this requires prior knowledge about the biofilm's bacterial composition, as the enzymes can be specific to EPS composition. Ultrasound has been explored by several labs as a means to break up the biofilm but has not proven to be successful for all bacterial species. While several methods hold promise, none yet show a clear path to a clinical setting.

Since the 1950s, magnetite nanoparticles have been used to wirelessly heat specific regions of the body in a process termed magnetic hypertherapy. To date, magnetic hypertherapy has been used almost exclusively for cancer treatment as a means to selectively ablate cancerous cells without damaging the surrounding tissue.

Thus, there is a need in the art for improved methods of biofilm treatment and prevention.

BRIEF SUMMARY

Discussed herein are various devices, systems and methods relating to a magnetically-sensitive coating that can be applied to various implanted medical devices for the treatment and prevention of biofilms. Upon implantation in the body, approximately 2-4% of medical devices become infected with a bacterial biofilm, despite decades of research into non-fouling surfaces and improved implantation protocols. These biofilm infections do not respond to pharmaceutical treatment (i.e., antibiotics), so the current standard of care is surgical removal of the device, along with any potentially infected adjacent tissue. After weeks or more of systemic antibiotic treatment, a new medical device is surgically implanted, with twice the rate of infection of the previous device.

Biofilms on implanted medical devices cause thousands of patients each year to undergo multiple surgeries to remove and replace the implant, driving billions of dollars in increased health care costs due to the lack of viable treatment options for in situ biofilm eradication. Remotely activated localized heating is under investigation to mitigate these biofilms.

These presently disclosed systems, methods and devices eliminate the biofilm infection without surgical intervention by instead exposing the biofilm to a localized thermal shock. This thermal shock is generated precisely at the surface of the device where the biofilm is growing by covering the device surface (before implantation) with a magnetically susceptible coating. When exposed to an alternating magnetic field, the coating generates heat, thermally killing any biofilm growing on it.

In certain implementations, the magnetically susceptible coating comprises a polymer. In various implementations, the polymer or polymers can include hydrophilic polymers such as poly(vinyl alcohol), poly(ethylene glycol) and the like; hydrophobic polymers such as poly(styrene), poly(methyl methacrylate), and others; and/or fluoropolymers such as poly(tetrafluoroethylene) and the like.

In various implementations, the implanted device can be an orthopedic implant, such as pins, plates, screws, rods, joints and the like; a dental implant; a valve, catheter, stent, shunt, or mesh; a cosmetic implant; and in certain implementations, devices such as pacemakers, defibrillators, and neuromodulators. In various implementations, certain devices can be magnetically shielded to prevent damage to the circuitry. In further implementations, components having low magnetic susceptibility, such as leads made of copper or gold, can also be coated with the disclosed coating.

In certain implementations, the coating is activated by the application of an alternating magnetic field, such as by way of a coil.

In various implementations, the coating is activated for about 5 minutes, though the activation can occur for less than a minute or more than 30 minutes in certain applications.

In certain implementations, the coating is configured to heat to a temperature between 50° C. and 80° C., though other temperatures are possible.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure.

Accordingly, the drawings and detailed description are to be regarded as illustrative in nature and not restrictive.

BRIEF DESCRIPTION OF THE DRAWINGS

FIG. 4 shows data related to alternating magnetic field mapping, according to certain embodiments.

FIG. 7 shows exemplary images of experimental apparatuses.

FIG. 9 shows SAR data for various compositions, according to certain embodiments.

DETAILED DESCRIPTION

Figure 1A:
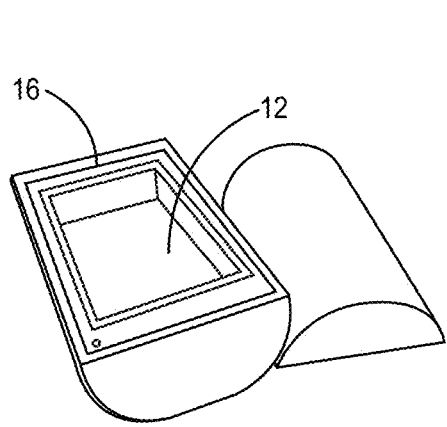
FIG. 1 shows exemplary images of the device, according to certain embodiments.

The various embodiments disclosed or contemplated herein relate to a magnetically-sensitive coating that can be applied to various implanted medical devices for the treatment and prevention of biofilms. In certain aspects, the coating can be applied to the surface of an implanted device, such as a catheter, valve, dental implant, replacement joint, or other device. In various implementations, the coating can then be "activated" through the application of a magnetic field to generate a specific heat over a period of time to deactivate the bacterial biofilm. In certain exemplary implementations, the coating is a magnetic nanoparticle/polymer coating.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, an "implantable medical device" is a device that has surfaces that contact tissue, bone, blood or other bodily fluids in the course of their operation, which are implanted into a body, and remain in the body for an extended period (e.g., greater than 28 days). Examples include, but are not limited to, stents, stent grafts, stent covers, catheters, artificial heart valves and heart valve scaffolds, venous access devices, vena cava filters, peritoneal access devices, and enteral feeding devices used in percutaneous endoscopic gastronomy, prosthetic joints and artificial ligaments and tendons.

Disclosed herein is the finding that device coatings comprising magnetically-sensitive components, such as magnetic nanoparticles ("MNP") can be used to treat or prevent biofilms on implanted medical devices. In various implementations, the coatings can be wirelessly activated by exposing them to alternating magnetic fields. Accordingly, in various implementations of the disclosed system, magnetic hyperthermia is used for treating medical implant infections via a polymer composite loaded with magnetite nanoparticles.

Disclosed herein is a system for disrupting a biofilm on a medical device that comprises an implantable medical device; a magnetically-sensitive coating on the surface of the implantable device comprising a polymer and magnetic particles embedded within the polymer; and a coil element capable of generating an alternating magnetic field, wherein the coil element is constructed and arranged to be capable of applying an alternating magnetic field to induce heating of the surface of the implantable device.

According to certain embodiments, the surface of the device has a plurality of zones wherein each zone has a distinct areal concentration of magnetic susceptibility. As used herein, "areal concentration of magnetic susceptibility" is the product of the total amount of magnetic material per area of the device surface times the material's average magnetic susceptibility. Areal concentration of magnetic susceptibility can be affected by the mass density of the magnetic particles, the thickness of the coating, or the magnetic susceptibility of the magnetic particles. For example, increasing the areal concentration of magnetic susceptibility can be achieved by increasing the coating thickness, increasing the mass density of the magnetic particles, utilizing magnetic particles with increased magnetic susceptibility (e.g., using superparamagnetic nanoparticulate magnetite instead of larger magnetite particles, or using certain cobalt materials instead of iron materials), or some combination of the foregoing.

In certain aspects, upon implantation of the device into the body of a subject, the areal concentration of magnetic susceptibility in each zone is proportional to its heat transfer coefficient to the body. As will be understood by persons having skill in the art, the various tissues of the body vary significantly in heat conductive properties. For example the amount of energy required to heat a surface contacting bone will be significantly less than the amount of energy required to heat a surface facing the lumen of a blood vessel. The instantly disclosed systems, methods and devices account for this by modifying the areal concentration of magnetic susceptibility according to the heat transfer coefficient of body tissue a given device surface will contact upon implantation of the device into the body of the subject.

In certain aspects, the areal concentration of magnetic susceptibility in zones perpendicular to the applied magnetic field lines is twice as large as the areal concentration of magnetic susceptibility in zones parallel to the applied magnetic field lines. According to still further aspects, the areal concentration of magnetic material in each zone is scaled by both its heat transfer coefficient to the body and its orientation to the applied magnetic field lines.

In certain aspects, the implantable medical device comprises a first zone and a second zone and wherein the areal concentration of the magnetic particles in the first zone is about twice the areal concentration of magnetic susceptibility in the second zone. According to certain further aspects, the alternating magnetic field comprises a magnetic axis that is substantially perpendicular to the first zone and substantially parallel to the second zone. According to still further aspects, application of the alternating magnetic field to the implantable device generates substantially equal increases in temperature in the first zone and the second zone.

In certain aspects of the system, the implantable medical device comprises a temperature sensor constructed and arranged to detect temperature changes on the surface of the implantable device. In exemplary embodiments, the system comprises a coil element controller that is configured to receive temperature information from the temperature sensor and to deliver alternating magnetic field until the surface of the implantable device reaches a predetermined temperature threshold.

Further disclosed herein is a biofilm-disrupting implantable medical device that comprises a device body having a surface; a coating on the device surface, the coating comprising a plurality of magnetic particles embedded within a polymer; and a temperature sensor constructed and arranged to detect changes in temperature on the surface and further configured to transmit temperature data to an operation system.

In certain aspects, the plurality of magnetic particles are nanoparticles, that is, less than 100 nm. In further aspects, magnetic particles are less than about 30 nm. While magnetic nanoparticles (MNPs) are referred to throughout this disclosure, larger particles (e.g. microparticles) are included within the scope of certain embodiments.

In certain implementations, the magnetic particles are comprises of materials such as iron, nickel, cobalt and the like. In certain implementations, the magnetically-susceptible material can be ferromagnetic, such as cobalt; ferrimagnetic, such as magnetite ($Fe_3O_4$) and maghemite; or superparamagnetic, such as single-domain nanoparticles of ferri- or ferromagnetic magnetic materials; or combinations thereof.

In certain aspects, the polymer is selected from the group consisting of hydrophilic polymers, fluoropolymers and hydrophobic polymers. In certain embodiments, the polymer is selected from the group consisting of poly(vinyl alcohol), poly(ethylene glycol), poly(styrene), poly(methyl methacrylate) and poly(tetrafluoroethylene).

In further aspects, the device surface defines at least a first surface zone and a second surface zone, wherein the areal concentration of the magnetic particles is substantially different between the zones. According to certain exemplary embodiments, the areal concentration of magnetic susceptibility in the first zone is about twice the areal concentration of magnetic susceptibility in the second zone.

Also disclosed herein is a method of disrupting a biofilm formed on a medical device implanted in a subject, where the device comprises a surface coated with plurality of magnetic nanoparticles dispersed in a polymer coating the surface of the device, the method comprising: applying an alternating magnetic field to the device; and monitoring the temperature of the surface of the device.

In certain aspects, the disclosed method further comprises the step of discontinuing the application of alternating magnetic field when the temperature reaches a predetermined threshold for a predetermined interval of time. In exemplary embodiments, the predetermined time is between about 30 seconds and thirty minutes. In further exemplary embodiments, the predetermined temperature threshold is between about 50 and 80 degrees centigrade. In still further exemplary embodiments, the alternating magnetic field is applied until the surface is heated to about 80 degrees for about 30 seconds.

According to certain embodiments, the AMF is applied until biofilm density is reduced to a predetermined threshold. In exemplary embodiments, the AMF is applied until biofilm density is reduced to a density of about $10^3$ CFU/CM2.

In certain aspects, the instantly disclosed method further comprises co-administering an antibiotic to the subject. In certain exemplary embodiments, the combination of antibiotic and alternating magnetic field produces a synergistic effect on the disruption of biofilm.

As best shown in the schematic of FIGS. 1A-E, in exemplary implementations of the system 10, an implanted medical device 12 has a magnetically-sensitive coating 14, such as a magnetic nanoparticle coating is implanted into the body. In one such implementation, the coating comprises a composite of hydrophobic polymer and magnetite ($Fe_3O_4$), though it is understood that other constituent parts can be utilized depending on the specific application.

Magnetite ($Fe_3O_4$) nanoparticles are ubiquitous in the field of magnetic nanoparticle (MNP) research for their medical applications in cancer treatment, drug delivery, and as a contrasting agent in diagnostic imaging. A widely exploited property of MNPs is their ability to wirelessly heat upon exposure to an alternating magnetic field (AMF); i.e., magnetic induction heating. On the nanoscale, (less than 30 nm) iron oxide particles exhibit superparamagnetic behavior affording them the ability to heat more efficiently than larger MNPs.

In various implementations, the use of a magnetic coating to induce thermal shock inside the body enables a treatment that focuses the energy directly on the implant surface, precisely where the bacteria are growing. The power generated by the composite is a result of the nanoparticle's propensity to convert alternating magnetic field (AMF) energy in to thermal energy. The presently disclosed implementations employ wireless heating of a biofilm, such as *P. aeruginosa*, using energy delivered from magnetic coating, such as a polystyrene (PS)/$Fe_3O_4$ nanoparticle coating. Experimental results demonstrating exemplary implementations of the system 10 follow.

In some implementations of the system, the coating can be activated by the application of an alternating magnetic field. In these implementations, the field can be applied by a magnetic coil.

Figure 1C:
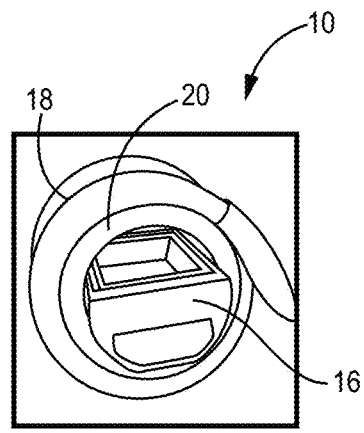
Figure 1B:
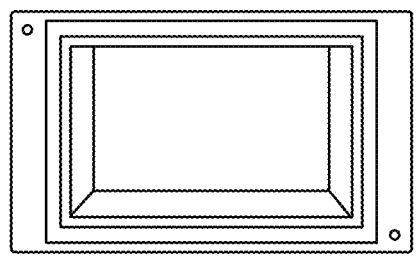
Figure 1D:
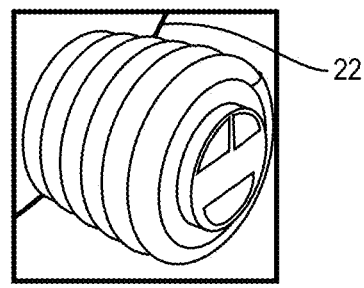
Figure 1E:
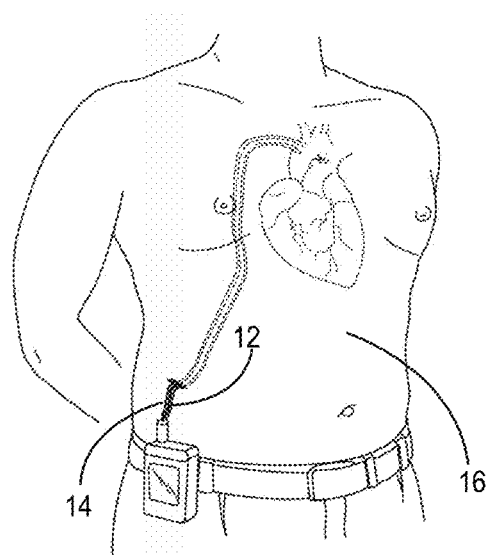

FIG. 1A depicts a circular chamber base and lid with hollow voids to insulate chamber from heat loss. The circular chamber mimics the body 16. FIG. 1B shows an overhead view of a coating 14 in the chamber base 16. In FIG. 1C, the chamber 16 is placed in 50 mm AMF coil 18 with insulating foam 20 between the coil 18 and chamber 16. In FIG. 1D, the chamber 16 is fully assembled in the coil 18 with a fiber optic temperature probe 22 passed through coil rungs and into the chamber 16. In FIG. 1E, a coated 14 catheter 12 has been inserted into a patient 16.

In certain implementations, an external device can be provided that is configured to detect the change in temperature and verify the safety and efficacy of the heating. In various implementations, this external device can detect the surface temperature of the coating. In various embodiments, the external device can assess changes in reflection frequency. In other implementations, these devices can detect the phase shift in the frequency, that is, by determining the lag in polarities between the applied field and the coating particles to determine the change in temperature.

In various implementations, the coating 14 can be "activated" to generate a controlled, temporary rise in temperature. In these implementations, the activation is achieved through the application of an alternating magnetic field, such as through the use of a coil 16. In various implementations, the coating can be activated for a specific period of time, such as five minutes or less, to generate sufficient heat, such as 80° C. to eliminate substantially all of the bacterial biofilm with limited damage to the adjacent healthy tissue. It is understood that in various implementations, the device 12 will also comprise magnetic shielding. It is further understood that in various implementations, the coating 14 applied to an device may vary in thickness or other parameters to ensure consistent heating. That is, in implants that do not have consistent surfaces, certain implementations of the coating will vary in thickness and/or composition to achieve consistent, controlled heat over these various aspects.

In certain implementations, the system 10 can be used to treat biofilm which has developed around an implant. In further implementations, the system can be used prophylactically to prevent the development of biofilms.

Example 1: Magnetic Nanoparticle/Polymer Composites for Medical Implant Infection Control The deactivation of bacterial biofilms requires higher power densities than can be supplied by previously developed polymer composites. These biofilm-specific coatings in turn require higher nanoparticle concentrations, where particle-particle and particle-polymer interactions play a significant role in the material performance.

The present example investigates the effect of several key design parameters on the resulting specific absorption rate ("SAR") of magnetite nanoparticle composites. Hydrophobic (poly(styrene), (PS)) and hydrophilic (poly(vinyl alcohol), (PVA)) polymer composite coatings were compared in both aqueous and non-aqueous solvents at multiple nanoparticle loadings and film thicknesses. In the present embodiments, heating rates up to 717 Wg$^{-1}$ Fe were observed in a typical (2.32 kA m$^{-1}$, 302 kHz) alternating magnetic field (AMF), achieving heating power densities up to 7.5 W cm$^{-2}$. To estimate in vivo power requirements, electrical resistance heating beneath a tissue mimic heat sink indicated a peak power requirement of only 4.5 W cm$^{-2}$ to achieve an 80° C. surface temperature in 15 s, demonstrating that these composites can exceed the power densities needed for applications such as treating bacterial infections on medical implants in situ. Polymer identity, solvent identity, and especially orientation within the magnetic field were shown to strongly affect the power density with effects that are interrelated.

In this application, an MNP-laden coating would wirelessly deliver heat from an implant surface of controllable composition, thus avoiding the dispersion problems faced in cancer therapy. Medical device associated infections account for 25.6% of all hospital-acquired infections in the U.S. This translates to an infection rate of 2-4% of all newly implanted devices. These infections are notoriously difficult to treat, forming dense bacterial biofilms which are resistant to antibiotics. Despite decades of research on preventative measures, the infection rate has not decreased and the standard of care is still explanation and replacement of the device, often in multiple surgeries. While not used for in situ medical implants, thermal deactivation of bacteria (e.g., pasteurization) has been employed at a variety of temperatures for over a century and thermal sterilization of medical and food processing equipment at >121° C. is standard. Thermal deactivation of *Pseudomonas aeruginosa* biofilms have recently been quantified at medically accessible temperatures (50-80° C.) and exposure times (1-30 min), showing population reductions of up to six orders of magnitude. This contribution details the development and characterization of a composite material which may be coated on a device surface prior to implantation to wirelessly deliver this thermal energy precisely to the infection on an as-needed basis.

The key parameter for such a material is its magnetic Specific Absorption Rate (SAR), defined as the thermal power provided by the magnetite composite film divided by the weight of iron in the film. SAR values reported in literature for magnetic fluid hyperthermia suspensions in water vary widely. For example, 15 nm, chitosan-coated, Fe$_3$O$_4$ nanoparticles will heat 50% more (119 W g$^{-1}$) than non-coated particles due to increased dispersion as a result of the hydrophilic coating.[24] Commercially available particles from Micromod exhibit a wide, but relatively low, range of heating (4-90 W g$^{-1}$), while 70 nm magnetic vortex nanorings demonstrate perhaps the most remarkable efficiency (2213 W g$^{-1}$).[25, 26] Most current hyperthermia suspensions have iron concentrations of 0.1 to 5 mg Fe mL$^{-1}$, which are then dispersed throughout the tissue. To provide the 4.5 W cm$^{-2}$ of heating power which may be needed for this application, even magnetite nanoparticles with a SAR of 1000 W g$^{-1}$ would need to be concentrated to 300 mg Fe mL$^{-1}$ in a 150 μm thick coating to provide this power density. The proposed material must have an MNP loading orders of magnitude larger than current materials, which may introduce significant particle-particle interactions and aggregation potential that complicate the design of an effective implant coating.

This application may also require mechanical moduli significantly different from current magnetic composites. Magnetite composites of poly(vinyl alcohol) (PVA), poly (ethylene glycol), poly(N-isopropylacrylamide), and poly (acrylamide) have all been reported to wirelessly heat in an AMF, though they are too soft in aqueous environments to be appropriate for orthopedic devices which comprise the largest share of the medical implant market.[15,27-30] This study compares composites of two opposing polymer matrices: hydrophilic PVA and hydrophobic poly(styrene) (PS), which is much more durable in aqueous conditions. We report the effect of several design parameters to produce composites which can supply large heating power densities from conventional AMF generators using materials commonly used in FDA-approved implants. In particular, magnetite concentration, coating thickness, polymer matrix, and coating orientation (relative to the applied AMF) were investigated. In addition, the amount of power needed to heat a surface to 80° C. for a conduction-only heat transfer scenario was quantified using a hydrogel tissue mimic. The SAR data was compared against these power density requirements to ascertain the composites' ability to meet realistic power demands.

Example 1: Materials and Methods

Magnetite synthesis. Magnetite nanoparticles were coprecipitated by reacting Fe$^{3+}$ and Fe$^{2+}$ in a 2:1 molar ratio in concentrated potassium hydroxide.[31] FeCl$_3$.6H$_2$O (6.46 g) and FeCl$_2$.4H$_2$O (2.38 g) (Sigma Aldrich) were dissolved in 18.1 MΩ·cm DI water (12.5 mL). A nucleated solution of iron oxide nanocrystals was prepared by diluting the iron solution (5 μL) with water (5 mL) followed by the addition of 15 M potassium hydroxide (10 mL) (Fisher Scientific) while vortexing. An ultrasonication probe (Cole-Parmer, model CV33) operating at 20 kHz and 300 W was submerged into the nucleated reaction vessel while simultaneously dispensing the iron salt solution into the vessel over a 90 s period using a 30 mL syringe fitted with a 22 AWG needle; black, iron oxide nanocrystals precipitated immediately. The reaction vessel was kept at 65° C. for 3 hr to allow for crystal growth via Oswald ripening.[32] Suspensions were rinsed by centrifuging for 5 min at 2400 rpm then decanted, probe-sonicated for 90 s, and resuspended with DI water (30 mL); this process was repeated an additional four times. Non-aqueous suspensions were rinsed an additional three times with 2-propanol (Fisher Scientific) followed by one rinse with toluene (Fisher Scientific).

Magnetite Characterization.

Particle Size and Morphology.

Iron oxide nanoparticle size and dispersion was observed via scanning electron microscopy using a Hitachi S-4800 electron microscope at 1.8 kV accelerating voltage. Polymer-magnetite composites were freeze fractured using liquid nitrogen and sputter coated with 1-2 nm of gold-paladium (5 mA, 60 s coating time, Emitech Sputter Coater K550) prior to imaging.

Figure 2:
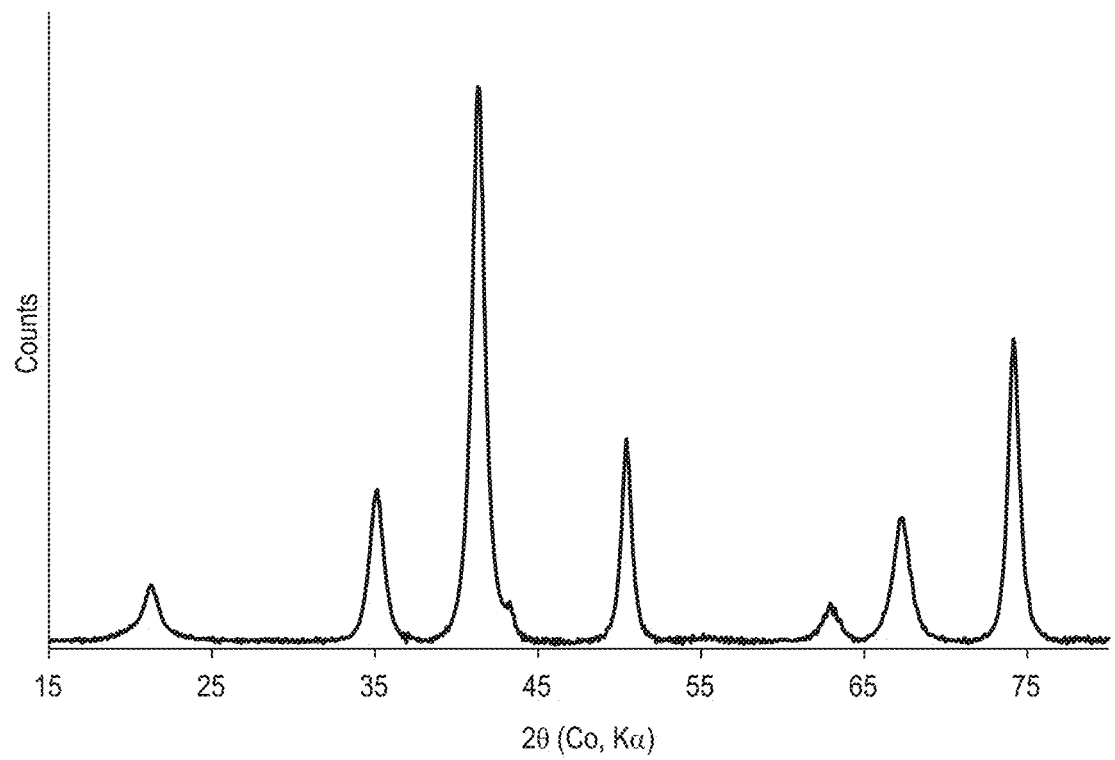
FIG. 2 shows data showing the pXRD pattern for magnetite sample dried from suspension, according to certain embodiments.
Figure 3A:
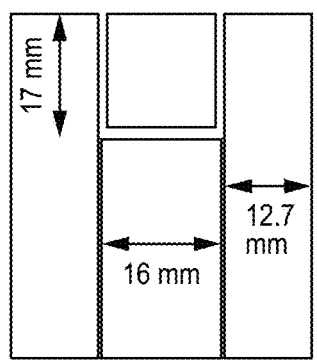
FIG. 3 shows exemplary images of experimental apparatuses.
Figure 3B:
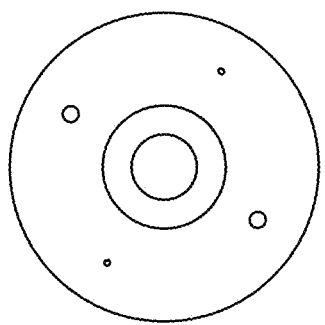
Figure 3C:
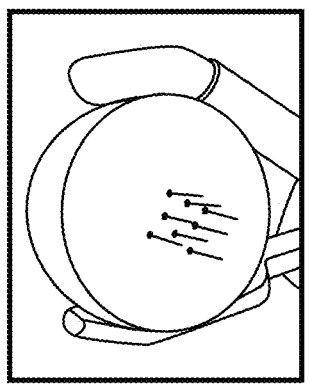
Figure 3D:
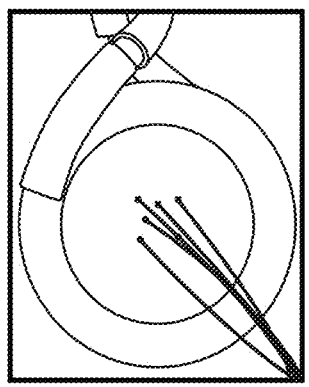

Iron stoichiometry. Magnetite oxidation was measured by determining the iron stoichiometry ($x_D$=Fe$^{2+}$/Fe$^{3+}$ which is 0.5 for pure magnetite and 0.0 for pure maghemite, γ-Fe$_2$O$_3$) for digested suspensions via the phenanthroline method.[33,34] pXRD patterns were collected on dry magnetite samples using a Rigaku MiniFlex II system equipped with a Co source (CoKα=1.7899 Å). Samples were analyzed from 15-80° 2θ with a 0.02° step size and a 3.0 s dwell time. The unit-cell length was calculated from fitted patterns using Jade 6 software (Materials Data, Inc.); patterns were smoothed, background subtracted, and Kα$_2$ stripped prior to fitting. The pXRD pattern for a typical magnetite sample from this study matches the peak localities of previously reported magnetite pXRD patterns as shown in FIG. 2.

Composite Synthesis.

Poly(Vinyl Alcohol) Composites.

Both polymer matrices were loaded with three distinct iron concentrations and three distinct thicknesses to produce nine composites per polymer. Magnetite-loaded poly(vinyl alcohol) (PVA) (99 mol % hydrolyzed, ~133,000 MW, Polysciences, Inc.) composites were prepared as films via solvent casting with an adjustable doctor blade at 750, 1250, and 1750 μm to produce the thin, medium, and thick films, respectively. PVA composites were prepared from rinsed magnetite suspensions (0.082 g/g±0.007) by dissolving 2.0, 4.0, and 8.0 g of PVA powder in suspensions at 90° C. for 10 min under continuous stirring to produce the 18, 28, and 40 wt % Fe films, respectively. Magnetite-PVA suspensions were cast on poly(tetrafluoroethylene) (PTFE) sheets, covered, and allowed to dry under ambient conditions for 24 hr. Composite films were vacuum dried for an additional 24 hr followed by hydrothermal cross-linking at 150° C. for 3 hr. Magnetite composites dried as uniform, black films with little to no surface defects. All samples were cut from the bulk film into circular coupons using a 12 mm diameter cork borer.

Poly(styrene) composites. Poly(styrene) (PS) (280,000 MW, Sigma Aldrich) composites were formed by dissolving 3.75, 7.5, and 15 g of PS resin in magnetite-toluene suspensions under continuous stirring for 60 min at room temperature to produce 9.0, 18, and 27 wt % Fe films, respectively. Magnetite-PS-toluene suspensions were allowed to rest for 30 min at room temperature to eliminate air bubbles, cast on PTFE, dried, and cut into circular coupons in the same manner as PVA composites.

Film thickness and iron concentration. Dried film thicknesses were measured using a hand-held micrometer (Mitutoyo, ±0.001 mm). The total iron concentration was measured in each coupon by digesting the composites in 8 M HCl (5 mL) for 24 hr, reducing all iron species to Fe$^{2+}$ with 10% hydroxylamine hydrochloride, complexing with 1% 1, 10-phenanthroline monohydrate, buffering with 3.7 M ammonium acetate, (Sigma Aldrich) and measuring the absorbance of 510 nm light with a UV/Vis spectrophotometer (Cary 50, Varian Inc.). The total weight of iron was divided by the total, dry coupon weight to calculate the wt % Fe in each composite; these values varied less than 3.4% for all coupons cut from the same film.

Specific absorption rate (SAR) measurement. Composites were heated using a 6-turn, 53-mm tall solenoid supplied by a 7.5 kW AMF generator (MSI Automation, Inc.) operating at 302 kHz with an rms current of 19.8 A at maximum power. Composites were tested in water (2.7 mL) and dodecane (2.5 mL) (Sigma Aldrich) to investigate the effect of swelling behavior on SAR for the PVA composites; PS composites did not swell in either solvent. Composite films were positioned both parallel and perpendicular to magnetic field lines to investigate the effect of orientation on SAR. Transient temperature measurements of the solvent surrounding the composite were collected using a minimum of six fiber optic temperature probes (0.170 mm OD, ±0.3° C., Opsens) and an 8-channel data acquisition device (USB-TEMP, Measurement Computing) using LabVIEW software (National Instruments). The solvent and composite were placed in a 3 mL plastic-well sample chamber which was placed in an insulating, 1.3 cm-thick styrofoam holder as shown in FIG. 3. Temperature measurements were collected every second for all temperature probes.

The magnetic flux density, B, in the AMF coil was calculated from the measured potential, ε, induced in the probe-coil (an 8-turn, 1.90 mm-diameter, 5 mil tungsten wire solenoid) using Equation 1 (all values in SI units), given by:

$$B_{probe} = \frac{\varepsilon_{probe}}{2\pi f N_P A_P}$$

This equation is derived for a solenoid from Ampere's and Faraday's Law where f is the AC frequency, $N_P$ is the number of turns in the probe coil, and $A_P$ is the cross-sectional area of the probe coil. Mapping measurements were taken at the center and around the circumference of the 16 mm-diameter sample chamber at four planes along its 17 mm height as shown in FIG. 4.

Conversion of the magnetic flux density in gauss to the magnetic field strength, H, in oersted is equal to unity in a vacuum; conversion from oersted to A m$^{-1}$ is a factor of 79.58.

Specific Absorption Rate.

All SAR values reported for this study are tabulated in Table 1, which includes the respective average film thickness and dry weight iron concentration.

TABLE 1

Magnetite/polymer composite characteristics and corresponding SAR values; n = 3.

| Polymer | Dry wt % Fe | Thickness (μm) | SAR (W g$^{-1}$) in water, ⊥ AMF | SAR (W g$^{-1}$) in dodecane, ⊥ AMF | SAR (W g$^{-1}$) in water, ∥ AMF | SAR (W g$^{-1}$) in dodecane, ∥ AMF |
|---|---|---|---|---|---|---|
| PS  | 8.9 ± 0.1  | 81 ± 1   | 289 ± 29 | 264 ± 32 | 489 ± 43 | 448 ± 26 |
| PS  | 8.9 ± 0.0  | 139 ± 2  | 311 ± 18 | 269 ± 17 | 451 ± 82 | 460 ± 35 |
| PS  | 9.3 ± 0.1  | 182 ± 0  | 329 ± 12 | 293 ± 15 | 485 ± 87 | 420 ± 30 |
| PS  | 18.7 ± 1.0 | 78 ± 2   | 242 ± 28 | 218 ± 14 | 439 ± 29 | 416 ± 26 |
| PS  | 19.5 ± 0.1 | 129 ± 8  | 261 ± 14 | 253 ± 11 | 488 ± 23 | 468 ± 32 |
| PS  | 16.6 ± 0.1 | 211 ± 2  | 282 ± 19 | 279 ± 17 | 498 ± 29 | 489 ± 53 |
| PS  | 27.4 ± 0.9 | 68 ± 3   | 209 ± 14 | 193 ± 35 | 499 ± 28 | 451 ± 41 |
| PS  | 26.4 ± 0.2 | 105 ± 5  | 239 ± 15 | 238 ± 36 | 547 ± 18 | 444 ± 28 |
| PS  | 26.1 ± 0.0 | 193 ± 19 | 250 ± 10 | 290 ± 48 | 562 ± 37 | 489 ± 26 |
| PVA | 17.6 ± 0.6 | 45 ± 6   | 322 ± 30 | 203 ± 29 | 626 ± 37 | 623 ± 44 |
| PVA | 17.6 ± 0.1 | 63 ± 3   | 329 ± 18 | 196 ± 15 | 636 ± 51 | 652 ± 48 |

TABLE 1-continued

Magnetite/polymer composite characteristics and corresponding SAR values; n = 3.

| Polymer | Dry wt % Fe | Thickness (μm) | SAR (W g$^{-1}$) in water, ⊥ AMF | SAR (W g$^{-1}$) in dodecane, ⊥ AMF | SAR (W g$^{-1}$) in water, ∥ AMF | SAR (W g$^{-1}$) in dodecane, ∥ AMF |
|---|---|---|---|---|---|---|
| PVA | 17.6 ± 0.1 | 98 ± 5 | 361 ± 15 | 221 ± 15 | 717 ± 33 | 681 ± 25 |
| PVA | 28.1 ± 0.2 | 39 ± 1 | 359 ± 28 | 141 ± 22 | 666 ± 53 | 611 ± 55 |
| PVA | 27.9 ± 0.1 | 68 ± 2 | 308 ± 29 | 193 ± 14 | 633 ± 26 | 561 ± 61 |
| PVA | 28.3 ± 0.4 | 109 ± 1 | 336 ± 19 | 153 ± 17 | 637 ± 29 | 640 ± 26 |
| PVA | 39.7 ± 0.1 | 40 ± 1 | 188 ± 18 | 116 ± 32 | 656 ± 37 | 618 ± 29 |
| PVA | 40.0 ± 0.2 | 68 ± 2 | 207 ± 12 | 123 ± 22 | 574 ± 36 | 586 ± 23 |
| PVA | 40.2 ± 0.5 | 97 ± 12 | 330 ± 50 | 100 ± 10 | 574 ± 46 | 714 ± 35 |

Figure 5A:
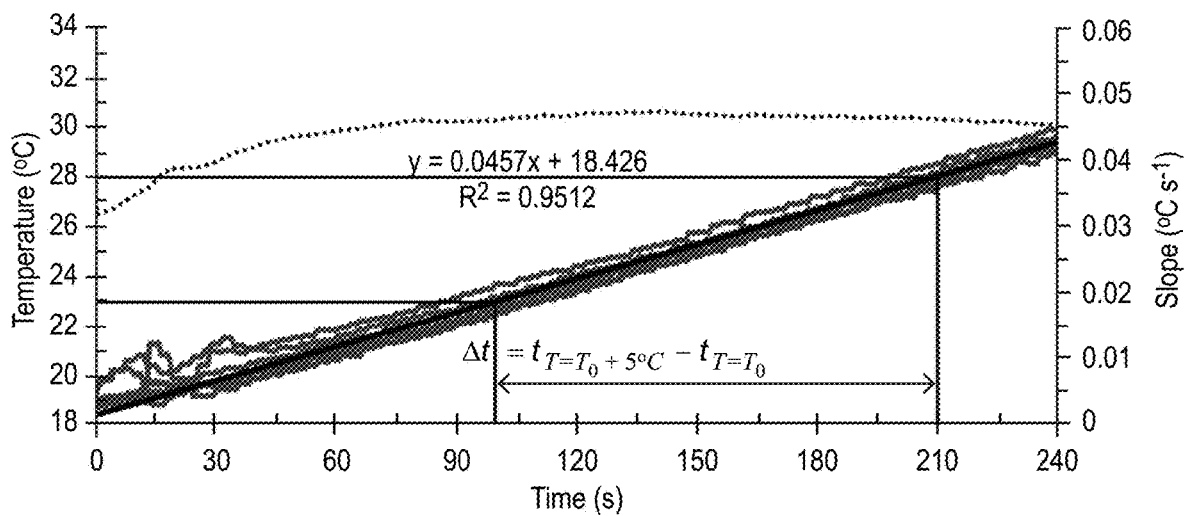
FIG. 5 shows temperature profile data, according to certain embodiments.
Figure 5B:
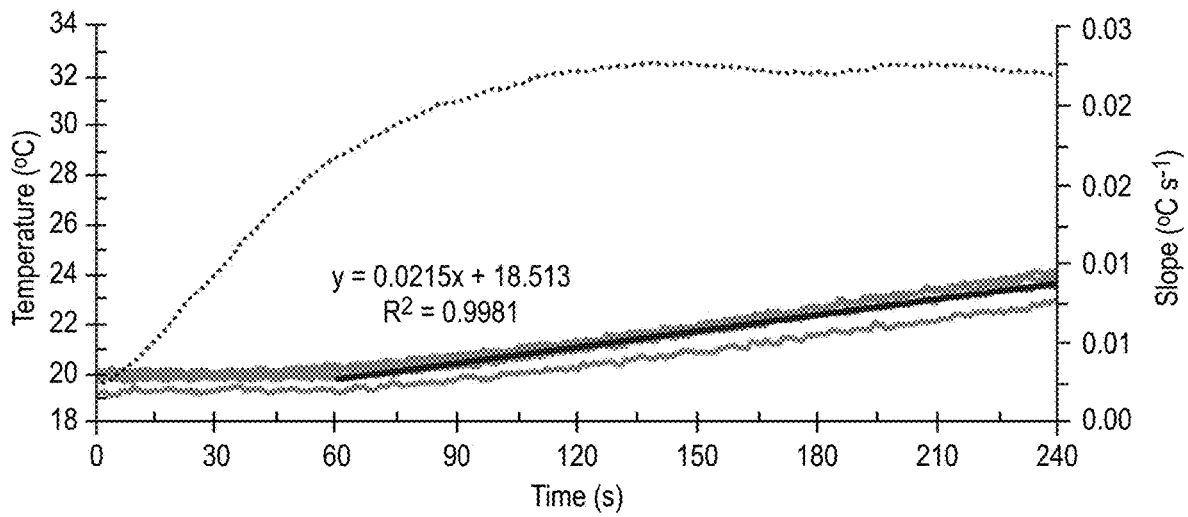
Figure 5C:
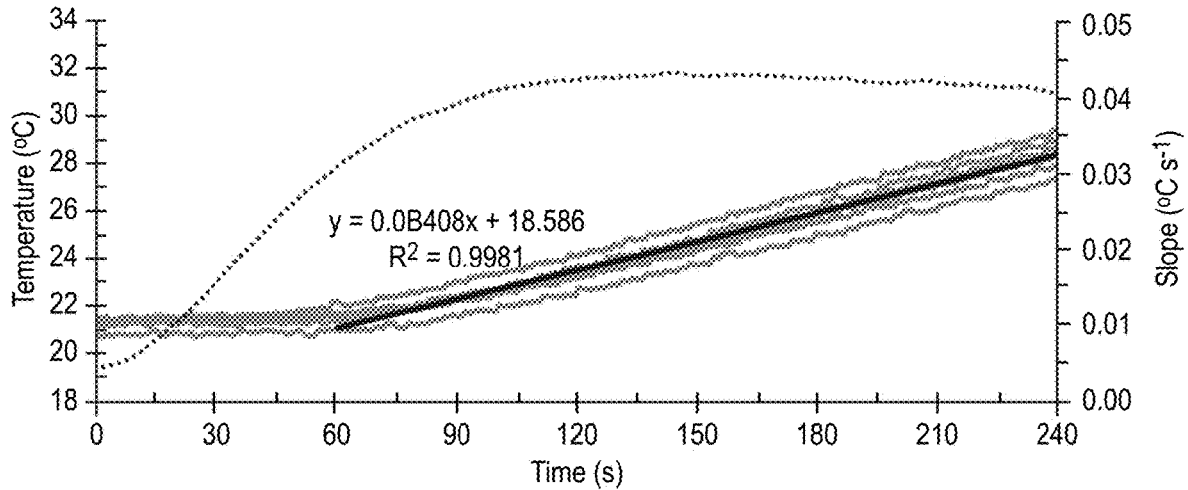

A typical temperature curve used to calculate SAR is shown in FIG. 5A. Iron-free controls were collected in the same sample chamber and coil at maximum power for a water-only trial (FIG. 5B) and a dodecane-only trial (FIG. 5C). These controls were subtracted from all slopes to account for the heat transferred into the coil from the induction coil for the same 5° C. temperature rise used to calculate m in Equation 2, below.

The SAR was calculated from transient temperature data by performing a simplified energy balance on the sample chamber assuming no heat loss to the environment, negligible spatial gradients in temperature, and negligible heat transfer resistance between the composite-solvent interface. SAR being given by Equation 2:

$$SAR = m \frac{c_p}{x_{Fe}} \text{ where } m = \frac{\Delta T_{avg}}{\Delta t}$$

where m is the slope of the $T_{avg}(t)$ curve calculated over a time period, $\Delta t$, in which the temperature in the sample chamber rose 5° C. Thus, for a large slope (m=0.3° C. s$^{-1}$) the time period for calculating m is less than the period for a small slope (m=0.03° C. s$^{-1}$) but over the same temperature range; i.e., $\Delta T$=5° C. for all SAR calculations. $T_{avg}$ is the average temperature recorded from all temperature probes; $c_p$ is the weighted heat capacity of both the solvent and plastic-well (3.50 J g$^{-1}$ K$^{-1}$ for all water trials and 2.2 J g$^{-1}$ K$^{-1}$ for all dodecane trials); $x_{Fe}$ is the weight fraction of iron in the heated sample chamber calculated from the wt % Fe and the total weight of sample well, solvent, and coupon in the sample chamber. All slopes were corrected for the amount of heat transferred into the chamber from the induction coil during the same 5° C. temperature rise used to calculate m via an iron-free control, as was shown in FIG. 5.

Alternating Magnetic Field Mapping.

To confirm the uniformity of the AMF generated by the induction coil, the magnetizing field strength, H, was measured throughout the sample chamber using a custom-built magnetometer probe. The probe measured the potential, ε, induced in the probe coil (an 8-turn, 1.90 mm-diameter, 5 mil tungsten wire solenoid) when placed in the AMF generated by the 52 mm-diameter induction coil. From the measured ε, the magnetic flux density, B, and the magnetic field strength, H, were calculated. Mapping measurements were taken at the center and around the circumference of the 16 mm-diameter sample chamber at four planes along its 17 mm height as shown in FIG. 4.

Heat Transfer Study in a Tissue-Mimic Hydrogel.

Experimental conduction models were performed in a custom built, 6.45 cm$^2$ by 15.2 cm long acrylic chamber insulated with poly(urethane) foam. An 8 wt %, PVA hydrogel crosslinked with glutaraldehyde (1:100 mol ratio to PVA, 50 wt %, Fisher Scientific) was cast as a tissue mimic throughout the entire chamber volume. A custom-cut 19.4 cm$^2$, 25 μm-thick nichrome foil (Ni80/Cr20, Goodfellow Corporation) heating element (path resistance=3.24 ohm) was used as the heat source; temperature variance across the middle 5.1 cm of the heating element was ±1.2° C., measured with an IR, thermal camera (FLK-TIR4-FT-20, Fluke). The power delivered to the heating element was controlled using a 0-18 V, 0-5 A programmable, DC power supply (1785B, BK-Precision) and LabVIEW software. Temperature feedback was measured using a 550 μm-diameter, polyimide-insulated thermistor probe (±0.1° C., Selco Products) positioned directly on the nichrome foil surface. PID feedback control was implemented to drive the surface temperature of the heating element to the desired setpoint within 15 s with less than 5° C. overshoot. Peak and steady state power requirements were measured for 50 and 80° C. surface setpoints.

Nanoparticle Dispersion in Polymer Composites.

Uniformly black, dry nanoparticle composites indicated excellent particle dispersion across the surface area of all films prepared here. This observation was supported by the low error (no greater than 3.4%) in film iron concentration measured via the phenanthroline method (see Section 2.3.3 in the main article) from coupons cut in triplicates at various locations from an approximately 10 cm by 20 cm film. Uniform film thickness was also achieved by solvent casting polymer/nanoparticle solutions on flat, poly(tetrafluoroethylene) sheets that were adhered to glass plates. This level casting procedure was performed with a 10 cm-wide casting blade which also contributed to a homogeneous particle dispersion across the film surface area.

Figure 6A:
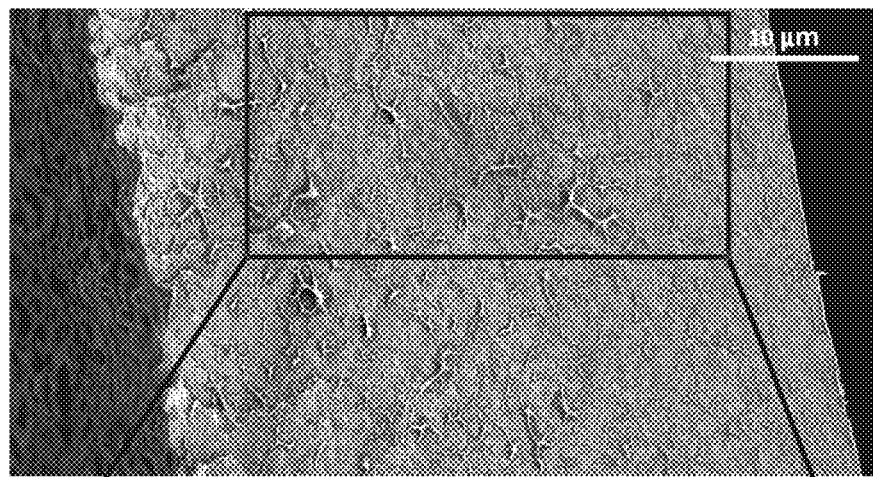
FIG. 6 shows exemplary S.E.M. images of nanoparticles, according to certain embodiments.
Figure 6B:
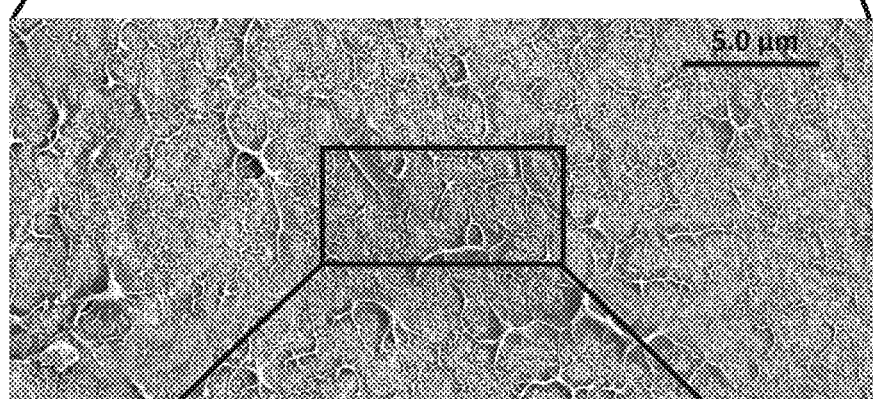
Figure 6C:
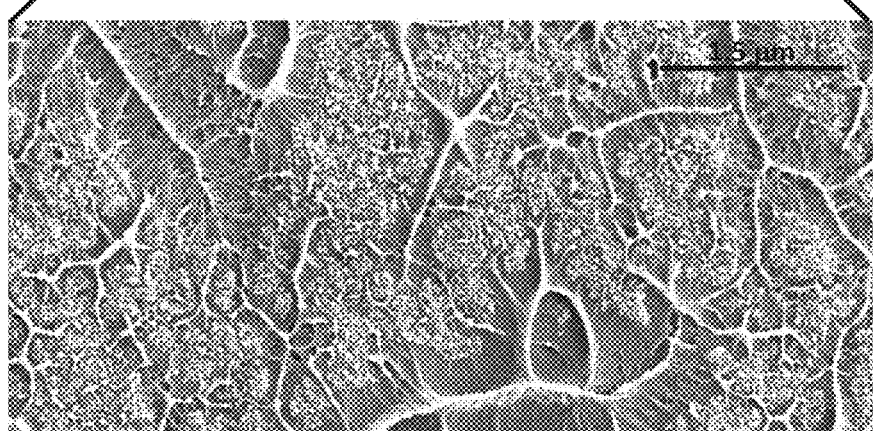

To address nanoparticle distribution in the thickness dimension of the films, FIG. 6 shows a cross-section of a typical PS film with progressive magnifications in SEM. In the bottom panel, individual particles in micron-sized aggregates are discernable; prior magnifications show that these features extend across the entire thickness of the film. This is unsurprising, as a Stokes' Law calculation for 20 nm iron oxide particles (5.1 g cm$^{-3}$ density) settling in an 8% w/w polymer solution (1.03 g cm$^{-3}$, 31.8 cP (determined by falling ball viscometer)) indicate a sedimentation of approximately 1 μm during the maximum 12 hours required for film drying. With aggregation this distance would decrease, though the effective viscosity of these non-Newtonian fluids under such low strain is likely to be orders of magnitude higher, and increasing quickly as the coating dries.

Heat Transfer Modeling.

All thermal models were performed in the 6.45 cm$^2$ by 15.2 cm long acrylic chamber shown in FIG. 7A, which also shows a cross-section of an approximately 2.5 cm-thick, PVA hydrogel in this chamber (FIG. 7B). FIG. 7C shows the nichrome foil heating element (2.54 cm by 7.62 cm) used to supply the temperature boundary condition for all setpoints; path resistance=3.24 ohm.

Example 1: Results and Discussion

Magnetite characterization. Particle morphology of superparamagnetic iron oxides is known to strongly influence SAR. Heating efficiency is best achieved with monodiperse particles at a particle size just below the superparamagnetic limit (20-30 nm). Scanning electron microscopy (SEM) indicated particle sizes less than 20 nm that were homogenously dispersed throughout the film in all composites reported (see the discussion of FIG. 6 above). Pure magnetite readily oxidizes at atmospheric conditions to maghemite in the absence of an encapsulating oxygen barrier and exhibits higher magnetization saturation (84 emu g$^{-1}$) than oxidized maghemite (74 emu g$^{-1}$). The iron stoichiometry for freshly synthesized magnetite suspensions used in this study was $x_D$=0.44±0.01 (n=2, measured via the phenanthroline method) demonstrating that the suspensions were largely unoxidized. The unit-cell length of a pure magnetite crystal is 8.396-8.400 Å. As magnetite oxidizes to maghemite, $Fe^{2+}$ occupied sites are vacated and the unit-cell length decreases; a=8.33-8.34 Å. Gorski and Scherer previously reported a linear trend of decreasing unit-cell length for decreasing iron stoichiometry in magnetite nanopowders: a=0.108$x_D$+8.341; $R^2$=0.914; n=9; where a is the unit-cell length and $x_D$ is the iron stoichiometry.[33] This trend can be used to interpolate the degree of oxidation of magnetite samples with reasonable accuracy from pXRD patterns. The calculated unit-cell length from the fitted pXRD pattern was 8.379 which corresponds to an iron stoichiometry of 0.352.[33, 34] Thus, some oxidation had occurred as a result of drying the suspensions in preparation for pXRD. Iron stoichiometry could not be measured for magnetite in composites due to unwanted oxidation of $Fe^{2+}$ at the higher acid concentrations needed to extract the iron from the polymer matrix.

AMF Mapping.

The measured H-field was 2.32 kA m$^{-1}$ at the center of the coil at maximum power. This value was in good agreement with the theoretical calculation of the field strength from the rms current in the coil, I, the coil length, L, and the number of turns in the coil, N; i.e., B=μNI/L=28.2 gauss=2.24 kA m$^{-1}$ where μ is the permeability constant equal to $4\pi \times 10^{-7}$ in SI units. FIG. 4 shows that the field strength varies less than 1.0% for the entire sample chamber volume.

Specific Absorption Rate.

Figure 8:
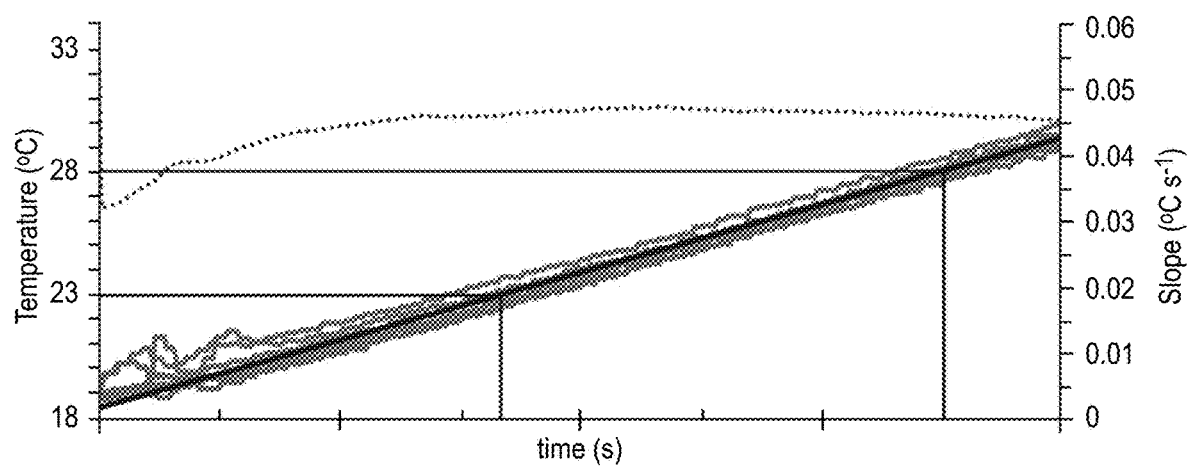
FIG. 8 shows transient temperature profile data.

A typical transient temperature curve for calculating SAR is shown in FIG. 8, demonstrating a linear increase in temperature over time varying less than 6.0% across the six locations in the chamber, with an $R^2$ value of 0.95.

FIG. 9 depicts all SAR values measured for this study, as are also demonstrated in Table 1, above. These values are organized to demonstrate differences in the measured SAR as a result of the samples' orientation to the applied AMF (parallel vs. perpendicular), their swelling behavior (water vs. dodecane), the type of polymer matrix (PVA vs. PS), and the iron loading (iron concentration and film thickness).

Orientation.

Figure 10A:
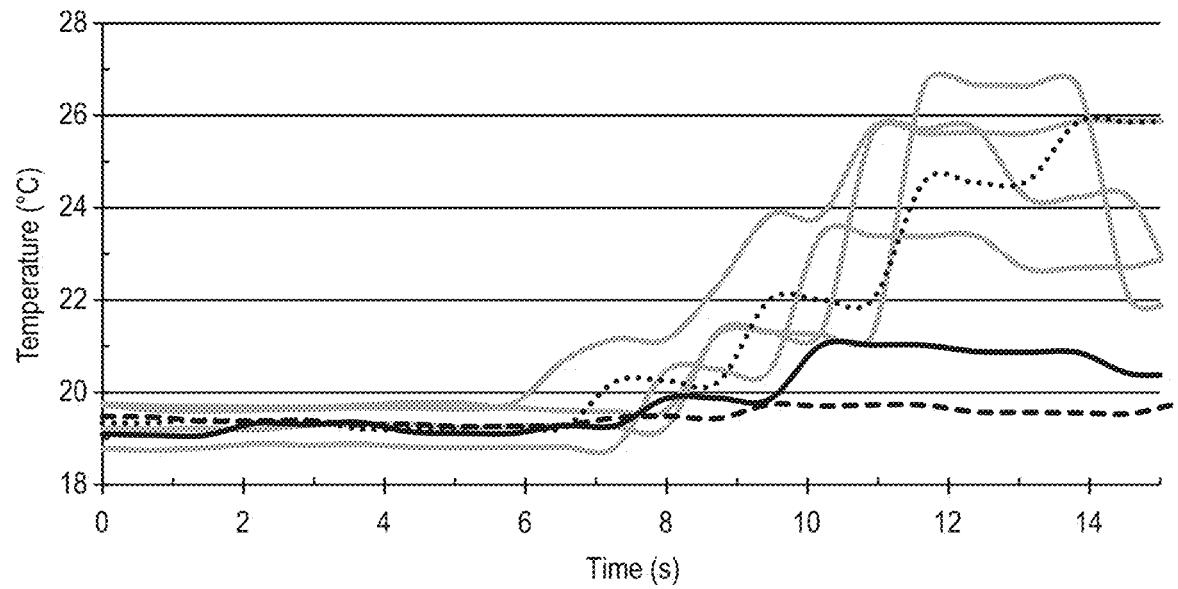
FIG. 10 shows surface heating data for compositions, according to certain embodiments.
Figure 10B:
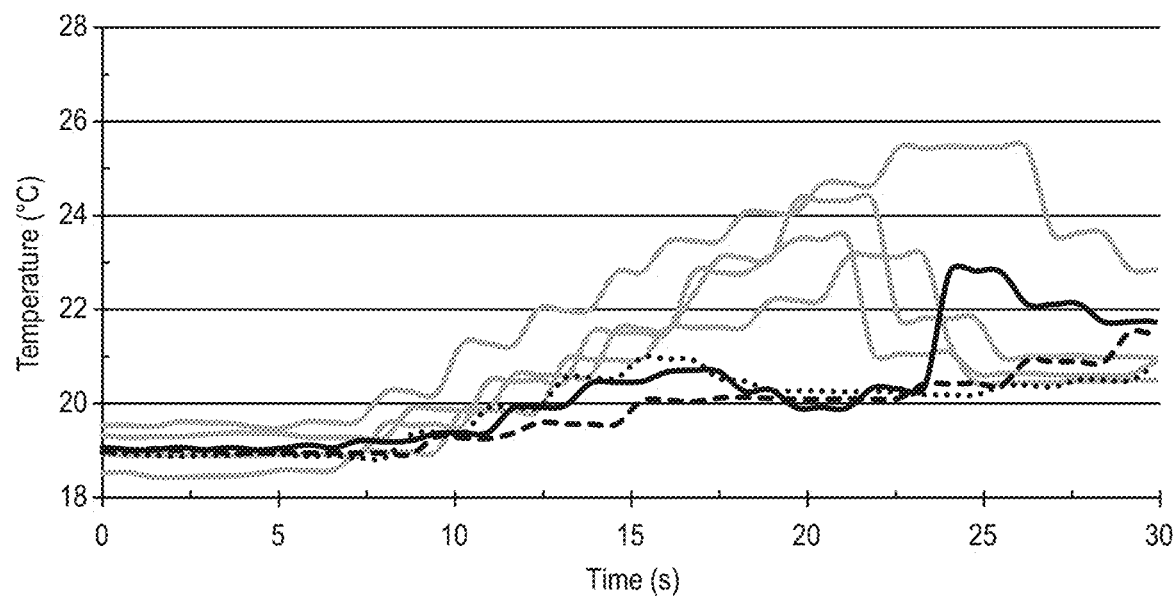
Figure 11A:
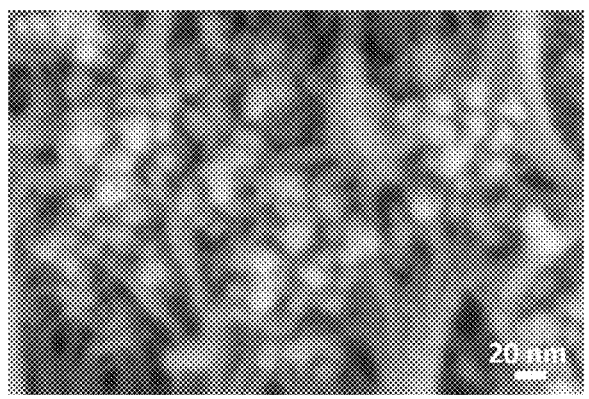
FIG. 11 shows exemplary SEM images for magnetite nanoparticles, according to certain embodiments.
Figure 11B:
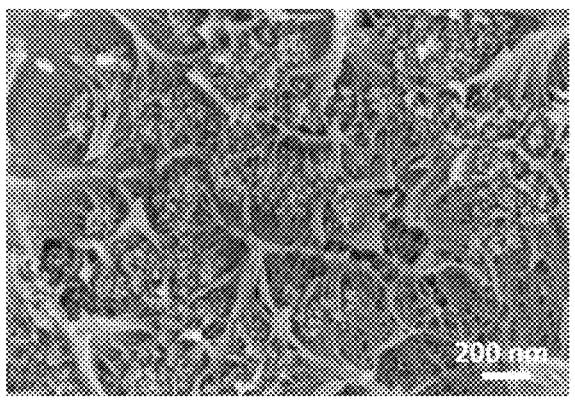
Figure 11C:
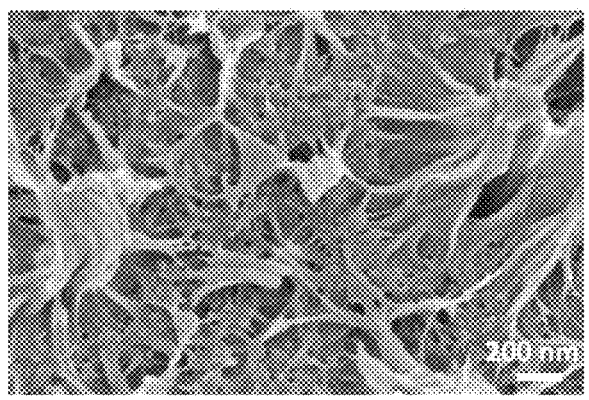
Figure 11D:
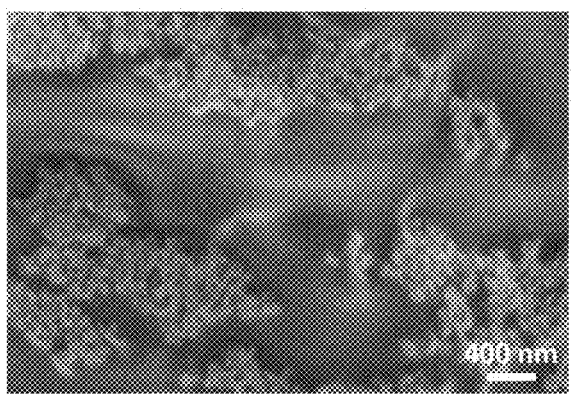

The change in the coating's orientation relative to the magnetic field results in the most dramatic difference in SAR. Films exhibited twice (1.96±0.50) the heating power when aligned parallel to magnetic field lines than the same film in the perpendicular orientation. The effect is even more pronounced in PVA/dodecane (FIG. 8D) where SAR increased by a factor of 4.19±1.54 due to the polymer's swelling capabilities as discussed elsewhere herein. While mapping indicated less than 1.0% variation in field strength across the 3 mL chamber volume (see FIG. 4), the field strength experienced by a given MNP decreases as more magnetically-susceptible material is situated between it and the generating coil. In this study, no MNP in a parallel-oriented coating has more than 210 μm of magnetic composite between it and the AMF source. By contrast, an MNP at the lateral center of a perpendicularly-oriented coating has 6.0 mm of magnetic composite between it and the AMF source. This effect was further observed by measuring the temperature of a composite's surface during the first 15-20 s of heating using spatially varied temperature probes across the coupon's surface as shown in FIG. 10. The center of the coating heated the slowest, despite having far less heat sink volume than the edge.

Swelling.

For PVA, the SAR of a hydrogel coating scales with its swelling factor in the perpendicular orientation. PS composites yield similar SAR values whether immersed in water or dodecane. As both solvents have comparatively little magnetic susceptibility and heat transfer/loss issues appear to be negligible, the lack of a solvent effect for the PS samples is not surprising. The SAR value of PVA composites doubles, however (factor of 1.96±0.68) when measured in water instead of dodecane in a perpendicular orientation. While PS does not swell in either dodecane or water, the PVA will swell to 62% of its dry weight in water, decreasing the iron concentration by a factor of 1.6-1.7 depending on the iron loading. This alters the SAR by changing the amount of magnetic material between a given MNP and the AMF source as discussed above. For PVA coatings in a parallel orientation, however, swelling has no significant effect. Here, the amount of magnetic material between an individual particle and the coil is effectively the same in either state due to the films' thinness (40-110 μm).

Polymer Type.

The composite's polymer type influences SAR even in the absence of swelling, and despite the fact that the matrices have no significant magnetic susceptibility of their own. PVA composites heated 1.27±0.24 times more than the PS composites across all solvent/orientation combinations except in dodecane in the perpendicular orientation for reasons discussed above. This is believed to be due to differences in MNP dispersion in different polymer matrices rather than polymer/particle interactions during heating. In the parallel orientation where the shielding effects discussed above are minimal, PVA composites outperformed PS composites by roughly the same factor whether they were swollen in water (1.3±0.22) or shrunken in dodecane (1.4±0.18) though the mechanical moduli, and presumably the particle adhesion, of the PVA changes drastically in those circumstances. At such high loadings, MNPs consistently formed 1-2 μm aggregates in both polymers as seen in the SEM images of FIG. 11. The most apparent difference between the two polymer composites is their structure where PS composites exhibited an open, porous network while MNP aggregates in PVA composites were distributed in a more continuous phase of polymer. Acid digestion of the PS composites revealed the polymer structure is retained in the absence of magnetite (FIG. 4C). The performance of a given polymer will change with advances in MNP dispersion techniques at high loading and in hydrophobic media.

Iron Loading.

Figure 12A:
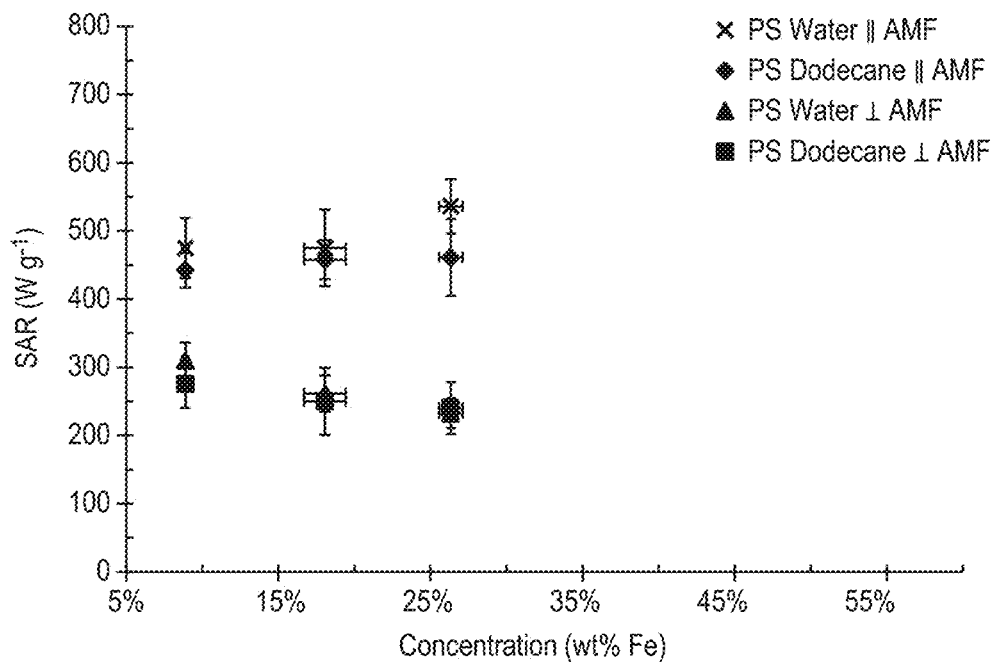
FIG. 12 shows SAR data for various composites, according to certain embodiments.
Figure 12B:
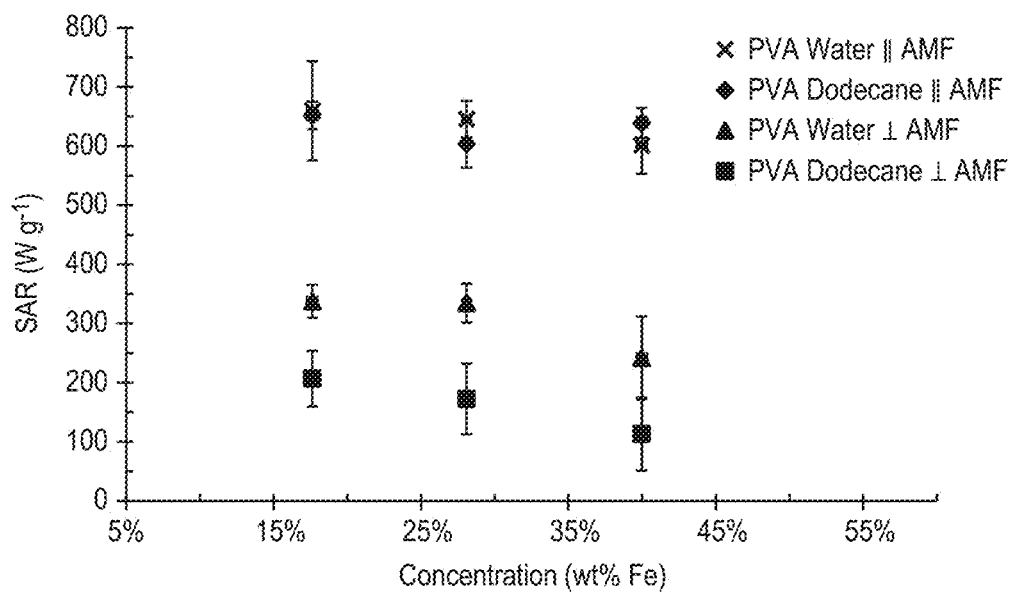
Figure 13A:
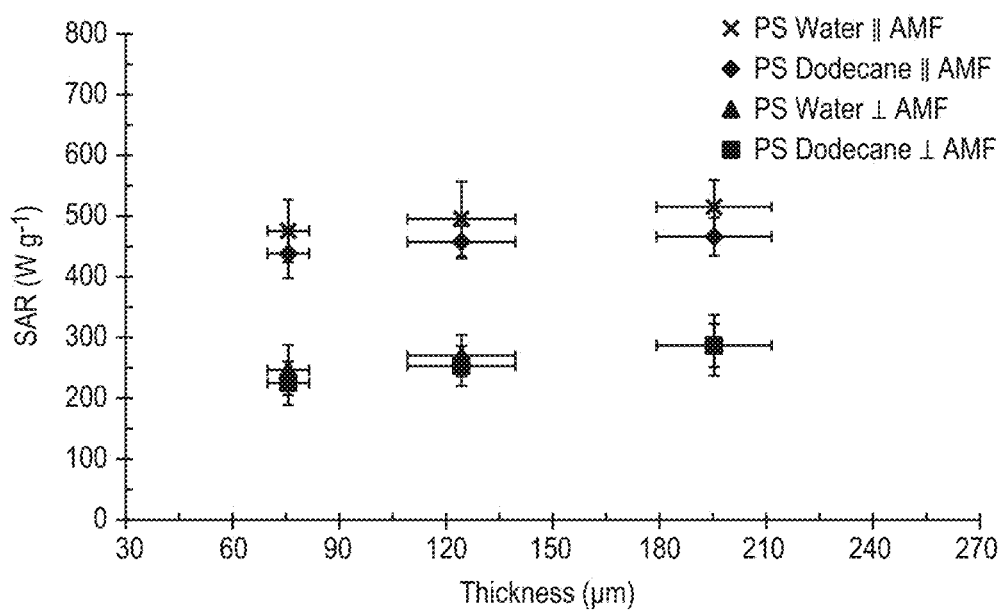
FIG. 13 shows SAR data for various composites, according to certain embodiments.
Figure 13B:
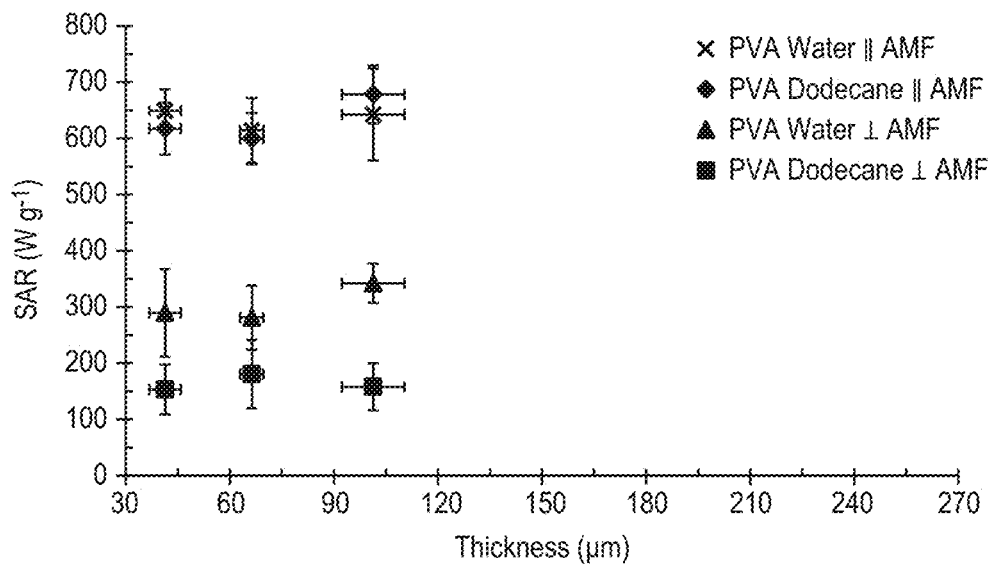

The practical implication of this result is not necessarily that improved MNP dispersion techniques are needed, however, as SAR values did not strongly change with iron loading across all solvents, polymers, and orientations investigated. When designing a coating for magnetic hyperthermia, this means that increasing the desired power density can be achieved simply by scaling up the magnetite loading proportionally, either through increased iron concentration or increased film thickness. However, based on the results discussed above, one would expect SAR to be independent of the iron weight percent in the parallel orientation and decrease with iron weight percent in the perpendicular orientation. Both effects may exist experimentally ($-0.38\pm0.12$ W g$^{-1}$% Fe$^{-1}$ in the perpendicular orientation but $+0.03\pm0.26$ W g$^{-1}$% Fe$^{-1}$ in the parallel orientation) but are too small to be significant across the range of iron concentrations investigated here as shown in FIG. 12. Similarly in FIG. 13, one might perceive an increase in SAR for increasing thickness, ($0.35\pm0.19$ W g$^{-1}$ µm$^{-1}$ for PS) but again this trend is not significant across the factor of three thickness variation investigated.

Power Density Requirements.

Figure 14:
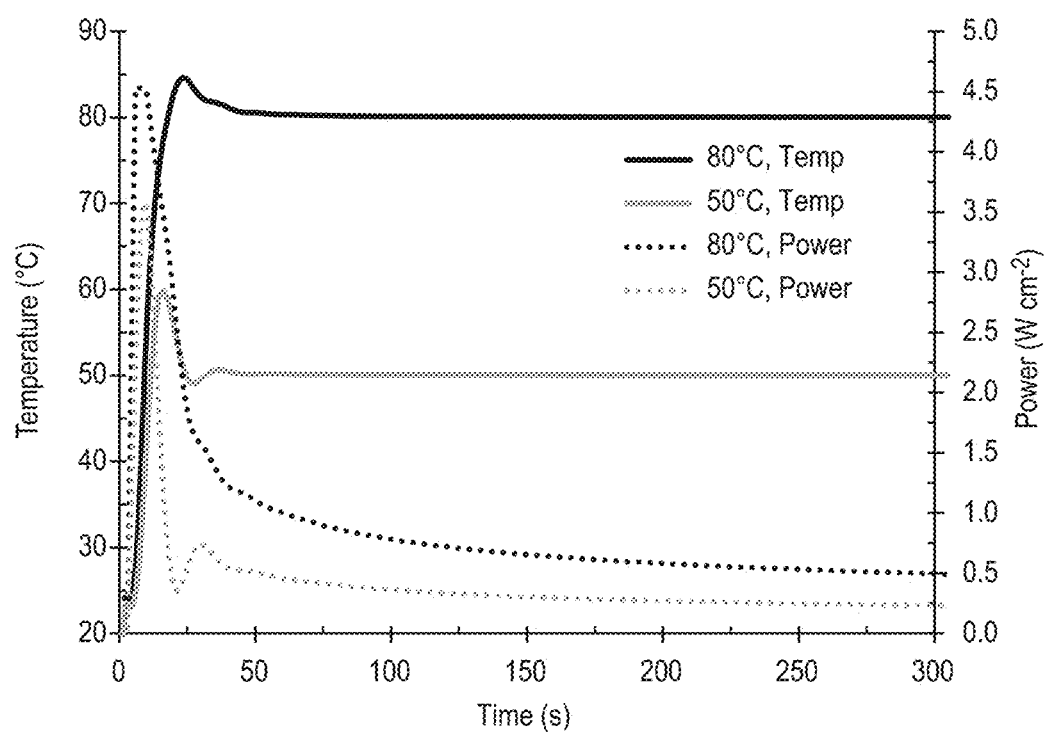
FIG. 14 shows transient temperature and power profile data, according to certain embodiments.

These results indicate that the heating power density of a composite coating can be scaled-up linearly by increasing the iron loading in the coating. To assess the extent to which this power would need to be scaled, an experimental thermal model was designed to estimate the power density which may be needed for clinical infection mitigation on medical implants. This was done using a resistive heating element to heat a surface beneath a conduction-only heat sink mimicked by a 2.54 cm-thick hydrogel tissue phantom. The steady and peak power delivered by the heating element was obtained from transient measurements using a PID temperature-feedback controller and a programmable power supply. A surface temperature setpoint of 80° C. was achieved in 15 s with 4.52 W cm$^{-2}$ of power; 0.50 W cm$^{-2}$ was needed to maintain this surface temperature for 5 min as shown in FIG. 14 which also plots the transient power density required for a less extreme, 50° C. setpoint.

Figure 15:
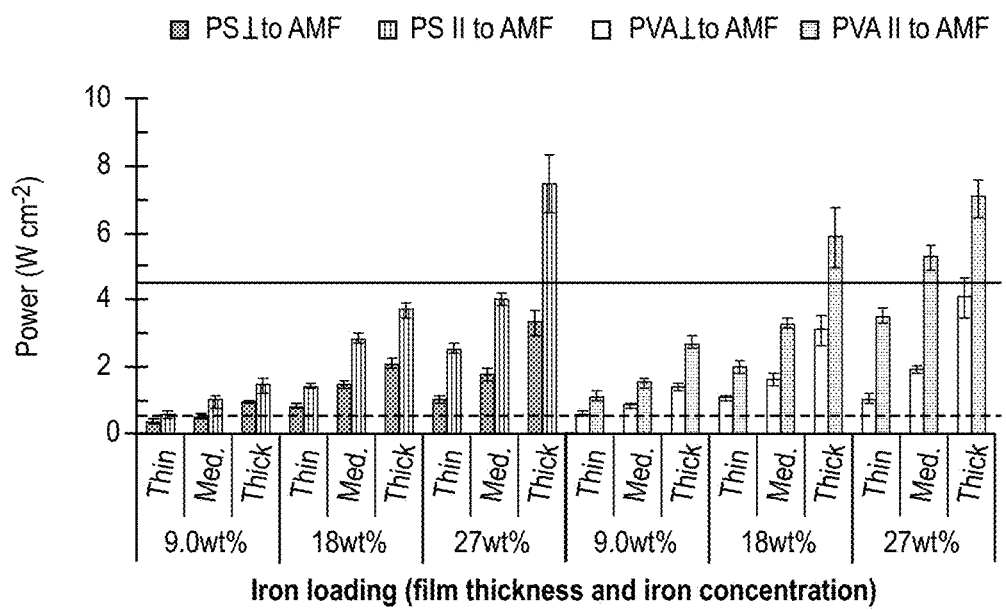
FIG. 15 shows power output for various composites, according to certain embodiments.

The 80° C. power requirements are plotted against the power output per unit area for all 18 magnetite composites measured in water for both orientations in FIG. 15. The highest iron-loaded PS and PVA composites are able to supply the maximum power demanded by the 80° C. conduction-only scenario. In the human body, higher power requirements may be necessary for a more extreme heat sink (e.g., a convection-driven scenario due to blood flow) which can be provided by thicker (greater than 211 µm) films and iron concentrations above 40 wt %.

Conclusions.

Magnetite suspensions have been administered for decades to ablate tumors in cancer patients, prompting a substantial body of research on biocompatibility and SAR optimization in fluid systems where large particle loadings in situ are challenging. Recent investigations on biofilm mitigation on medical implants have prompted interest in magnetite/polymer coatings which can wirelessly supply on-demand heating power precisely at the biofilm surface. The power density for this application, as investigated here, requires particle concentrations orders of magnitude greater than in most previous studies. While such loadings are easily accessible in a composite coating, the increased potential for particle-particle interactions and aggregation within a solid heterogeneous composite of defined geometry makes the design of such coatings much less straightforward. This example has demonstrated the orientation of the coating with regard to the field lines of the AMF has a strong impact on the observed SAR. This finding is particularly important as it implies that simply coating a three-dimensional device with a uniform film will not result in uniform heat generation, let alone uniform temperature, even within a uniform AMF. Each coating surface must be designed based not only on the adjacent heat-sink conditions, but also on any adjacent magnetically-susceptible material and its position relative to the applied AMF. Increasing the power density at any specific location, however, requires only that the total iron loading be scaled proportionally. The composite matrix, though not itself magnetically susceptible, still influences the observed SAR, due primarily to its degree of swelling and the degree to which particles can be evenly distributed at large (2-10% v/v) concentrations. Coatings using biocompatible polymer matrices generated sufficient heating power density to achieve 80° C. in 15 s beneath a tissue phantom heat sink. Subsequent improvements in theoretical design of these coatings will require more extensive experimental investigation on the dispersion of MNPs at large concentrations in polymers approved for medical use.

Example 2: Thermal Shock Susceptibility of *Pseudomonas aeruginosa* Biofilms

Thermal shocks were applied to *Pseudomonas aeruginosa* biofilms grown in different conditions and growth media types to determine the feasibility of thermal mitigation for the subsequent biofilms. It was found that the *P. aeruginosa* biofilms grown in different media were substantially similar, while the biofilms grown in different conditions changed the thermal susceptibility of the bacteria. The biofilms grown in drip flow reactors were more susceptible to lower temperatures than biofilms grown on a shaker table. However, at higher temperatures the biofilms showed similar trends in susceptibility to the thermal shock indicating that heating an implant at higher temperatures for short periods of time may be the most uniform way to mitigate these biofilms in situ. The introduction of thermal shock applied directly to the implant's surface to mitigate biofilms could obviate thousands of surgeries and save billions of dollars spent on explanation, recovery, and re-implantation.

Elevated temperature has proven to be a reliable approach for eliminating bacterial populations. Heating protocols for planktonic bacteria have long been established at a variety of temperatures and exposure times, and more recently, the decrease in colony forming units (CFU) within a bacterial biofilm has been quantitatively correlated to the degree and duration of thermal shock, according to Equation 3:

$$(CFU/cm^2) = (CFU/cm^2)_0 * 10^{-0.079(T-37)} * t^{-0.044(T-37)}$$

where T is the temperature in degrees Celsius, t is the exposure time at that temperature in minutes, and (CFU/cm$^2$)$_0$ is the original population density of the bacteria in the biofilm. If an implanted medical device has been coated with a magnetically susceptible material, this heat may be delivered wirelessly via an alternating magnetic field to the precise location where the biofilm is growing.

The bacterial cell death described by Equation 3 covered a temperature range from 37° C. to 80° C. with exposure times ranging from 1 to 30 minutes. In order to quantify the dramatic CFU decrease within this range (up to six orders of magnitude) the biofilms used in that study were grown in tryptic soy broth (TSB) for 1 day in a drip flow reactor to obtain initial CFU loads of nearly 10$^9$ CFU/cm$^2$ believed to be far beyond the CFU density typically observed on an infected medical implant. To determine how these previous findings on the correlation of temperature exposure to bacterial density apply under broader circumstances this study cultivated mature (4 day) biofilms with significantly lower initial bacterial loads (~$10^7$ CFU/cm$^2$) and architecture using a shaker table protocol. Moreover, biofilms were investigated using four different growth media: TSB, Mueller Hinton broth (MHB), a minimum glucose medium (GM), and a medium more commonly used for mammalian cell culture. Consistent with prior studies, these trials used biofilms of *Pseudomonas aeruginosa*, a well-studied, model organism. *P. aeruginosa* is the third most common bacterium to cause etiologic infections of orthopedic implants, making up 9.2% of all the medical implant infections and its systemic infection mortality (38.7%) is at the top of the range for nosocomial infections.

Example 2: Materials and Methods

Inoculum.

*Pseudomonas aeruginosa* PAO1 (15692, American Type Culture Collection, Manassas, Va.) stores in glycerol were thawed and streaked onto agar plates (Difco Nutrient Agar, Sparks, Md., USA) and incubated inverted for 24 hours at 37° C. Two colonies were then removed and placed into 5 mL of sterilized (autoclaved at 121° C. and allowed to cool prior to use) tryptic soy broth (TSB, BD Bacto, Sparks, Md., USA) and grown for 24 hours at 37° C., obtaining an average of 2.12×10$^9$±0.07×10$^9$ CFU/mL.

Biofilm Growth and Medium Preparation.

Glass microscope slides (75 mm×25 mm×1 mm), fully frosted on one side, were placed individually in polystyrene 4-well dishes (Thermo Scientific Nunc, Rochester, N.Y., USA) along with 333 µL of the inoculum and 5 mL of media per well, then sealed with parafilm. These dishes were placed on an orbital shaker table (VWR Standard Orbital Shaker, Thorofare, N.J., USA) set at 160 rpm in an incubator at 37° C. for 96 hours. Four different media were used, tryptic soy broth (TSB, BD Bacto, Sparks, Md., USA), Mueller Hinton broth (MHB, Difco, Sparks, Md., USA), a minimum glucose medium (GM), and a mixture containing 90% by volume minimum essential media a with no nucleosides (MEM-α, Gibco Life Technologies) mixed with 10% by volume fetal bovine serum (FBS, Life Technologies) to better simulate the growth anticipated in a body.

Thirty grams of TSB powder were dissolved into a liter of de-ionized water and heated for 10 minutes in a 700 W microwave. Powder MHB was dissolved at a concentration of 21 g per liter of de-ionized water and similarly heated for 10 minutes in a 700 W microwave. Both TSB and MHB were then autoclaved at 121° C. to ensure sterility. The minimum glucose medium (GM) was made by mixing 1.44 mg ferrous sulfate heptahydrate, 24 mg magnesium sulfate, 2.7 g potassium phosphate dibasic, 2.7042 g glucose, 4.3 g potassium monophosphate, and 5.232 g 3-(N-morpholino) propanesulfonic acid into 500 mL of de-ionized water and filter sterilized (all chemical components purchased from Fisher Scientific, Waltham, Mass., USA). The 90% MEM-α and 10% FBS (MEM-α/FBS) mixture was made by combining the two components (both liquids) in a 9:1 ratio by volume, MEM-α to FBS, and then filter sterilizing.

Heat Shock Procedure. After the 96 hour growth period the biofilms and their underlying glass substrates were transferred to a preheated 4-well dish containing 5 mL water per well whose temperature was maintained by a water bath (Isotemp 3013P, Fischer Scientific, Pittsburgh, Pa., USA) at the target temperature. After the target exposure time the substrate and biofilm were swiftly transferred to the recovery plate, another 4-well dish containing 5 mL water in each well at room temperature. The temperatures studied were 50, 60, and 80° C., with controls at 37° C. The different exposure times investigated were 1, 5, and 30 minutes.

Enumeration.

After the thermal shock, the 4-well dish containing the recovered biofilms was wrapped in parafilm and sonicated for 10 minutes at 45 kHz in a VWR Symphony 9.5 L sonicator (Radnor, Pa., USA). The homogenized suspension was then serially diluted in tenfold increments and spot plated using 10 µL droplets on agar plates (Difco Nutrient Agar, Sparks, Md., USA). After 5 minutes to let the droplets adsorb the plates were inverted and incubated at 37° C. for 20-24 hours before counting the colony forming units (CFU). The CFUs were then converted into a more relevant logarithmic density value given by Equation 4:

$$\log\left(\frac{CFU}{cm^2}\right) = \log\left[\frac{(\text{plate count}) * 10^{\text{dilution factor}} * \left(\frac{5 \text{ mL}}{0.1 \text{ mL}}\right)}{18.75 \frac{cm^2}{\text{slide}}}\right]$$

where $$\log\left(\frac{CFU}{cm^2}\right)$$

is the reported value, the plate count is the number of CFUs counted, the dilution factor is the amount of dilutions (0.1 mL in 1 mL) needed to obtain the countable CFU set used, 5 mL represents the total volume into which the bacteria were sonicated, 0.1 mL is the sampled volume of the resulting suspension, and 18.75 cm$^2$ is the surface area of the biofilm's substrate.

Confocal Imaging.

For confocal microscopy imaging, non-enumerated biofilms in the recovery plate were dyed using the Filmtracer LIVE/DEAD Biofilm Viability Kit (Molecular Probes, Inc., Eugene, Oreg., USA). This is a membrane permeability assay, in which Syto9 (excitation wavelength 488 nm, emission wavelength 500 nm, green) can enter all cells and fluoresce when bound to nucleic acid, while propidium iodide (excitation wavelength 568 nm, emission wavelength 635 nm, red) can only access cells with damaged membranes, displacing Syto9 in those cells. With non-overlapping emission and excitation peaks, these dyes allow clear differentiation between the dead and live bacteria via confocal microscopy. In each well containing a biofilm 30 µL of Syto9 was added along with 30 µL of propidium iodide. Biofilms grown in the drip flow reactor (DFR) were imaged using an upright Bio-Rad Radiance 2100 multiphoton/confocal microscope (Hemel-Hempstead, United Kingdom) with a 40× dip lens, while biofilms grown on the shaker table were inspected using a Zeiss LSM 710 confocal microscope (Oberkochen, Germany) with a 63× dip lens. Both microscopes used confocal settings with an argon laser to excite the propidium iodide and a helium-neon laser to excite the Syto9 dye. Biofilms were scanned in 1 µm vertical increments from bottom to top, with each laser scanning the entire plane separately at each increment to decrease any overlap in the resulting excitations and emissions. Images were collected in a 1024×1024 pixel array and the resulting images were post-processed in the Java-based ImageJ processor (freely available from the NIH website at http://imagej.nih.gov/ij).

Statistical Analysis.

Statistical analysis of the enumeration results was performed in GraphPad Prism 6. Averages and standard deviations were obtained via arithmetic calculations of log (CFU/cm$^2$) values. A two way ANOVA with a 95% confidence interval set was used to compare the means. The graphs were produced in GraphPad Prism 6 based on the calculated arithmetic mean and standard deviation.

Example 2: Results

Difference in Biofilm Architecture and Population.

Figure 16A:
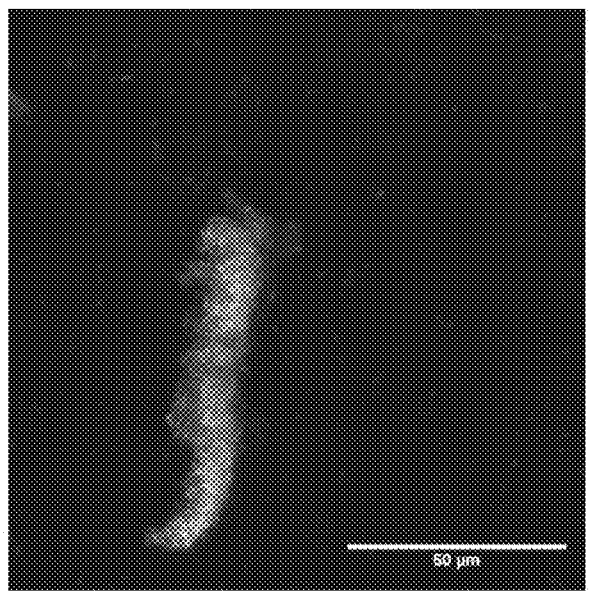
FIG. 16 shows confocal images of various biofilms.
Figure 16B:
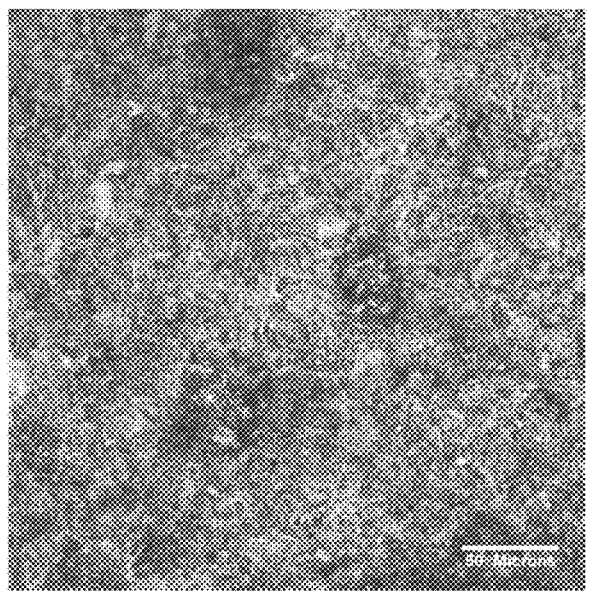

FIGS. 16A-B depict confocal microscopy comparison of shacker table to drip flow reactor growth. Both images are composite images formed by stacking each series of biofilm image slices. (A) The shaker table-grown biofilms show less uniform cell growth on the microscope slide's surface with fewer live cells, imaged using a 63× water dip lens, than seen in (B) the drip flow reactor-grown biofilms, imaged using a 40× water dip lens. Red indicates dead bacterial cells while green indicates live bacterial cells.

Biofilms grown on a shaker table for 96 hours were starkly different from the biofilms grown in a drip flow reactor (DFR) for 24 hours in both morphology and amount of colony forming units (CFU) even when using the same growth medium, TSB, for the same organism, P. aeruginosa. FIGS. 16A-B depict the two composite confocal image renderings of each biofilm with the live cells fluorescing green with Syto9 dye while the dead cells contain red-fluorescing propidium iodide due to poor membrane integrity. The DFR biofilms had bacteria more densely covering the microscope slides' surface area, typically 100 µm thick with plumes up to 150 µm (FIG. 16B). The shaker table biofilms were more dispersed across the microscope slides with fewer adhered bacteria in between the biofilm plumes ranging only up to 50 µm in thickness (FIG. 16A). Quantitatively, the CFU population density in the shaker table-grown biofilms was one hundred fold smaller ($10^{6.64\pm0.53}$ CFU/cm$^2$) than the DFR-grown biofilms ($10^{8.55\pm0.32}$ CFU/cm$^2$).

Thermal susceptibility.

Figure 17:
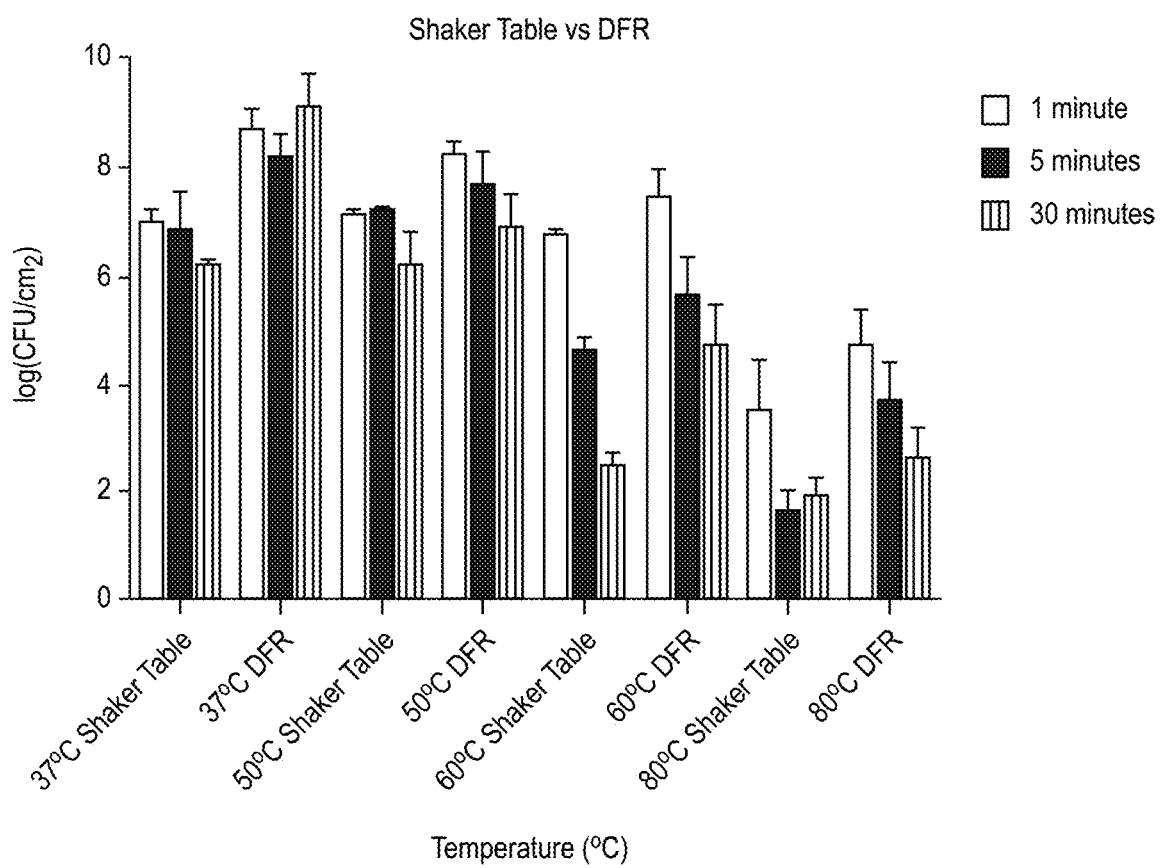
FIG. 17 shows thermal susceptibility data, according to certain embodiments.

FIG. 17 shows shaker table vs. drip flow reactor heat susceptibility. Biofilms were grown in tryptic soy broth and thermally shocked at various temperatures, and counted on agar plates to determine the CFU for both the shaker table and DFR growth methods. Biofilms grown on the shaker table and grown in a DFR. Both were heat shocked at temperatures of 37, 50, 60, and 80° C. and compared to determine their relative differences and similarities. Error bars represent the standard deviation.

The shaker table biofilms also demonstrated significantly different susceptibilities to the thermal shock than seen in the DFR biofilms, as shown in FIG. 17. While the CFU viability count in DFR biofilms decreased by 0.3-1.7 orders of magnitude depending on exposure time at 50° C., the shaker table biofilms showed no susceptibility, maintaining the same CFU/cm$^2$ values even after 30 minutes of exposure time. At 60° C., however, the shaker table biofilms showed a sharp dependence on exposure time, with no discernable effect at 1 minute of exposure and increased cell death when exposed for longer time periods. At five minutes of exposure to the 60° C. heat the viable bacterial population dropped by two orders of magnitude and at 30 minutes of exposure time the CFU/cm$^2$ count dropped by four orders of magnitude. These decreases are comparable in magnitude and more time dependent than those exhibited by DFR-grown biofilms subjected to the same conditions. Similarly, the 80° C. thermal shock on the shaker table biofilms had 3.2 to 5 orders of magnitude decrease in the viable cell counts, below the quantification limit of the experiments, in some cases yielding no CFU at all.

Growth media effects.

Figure 18:
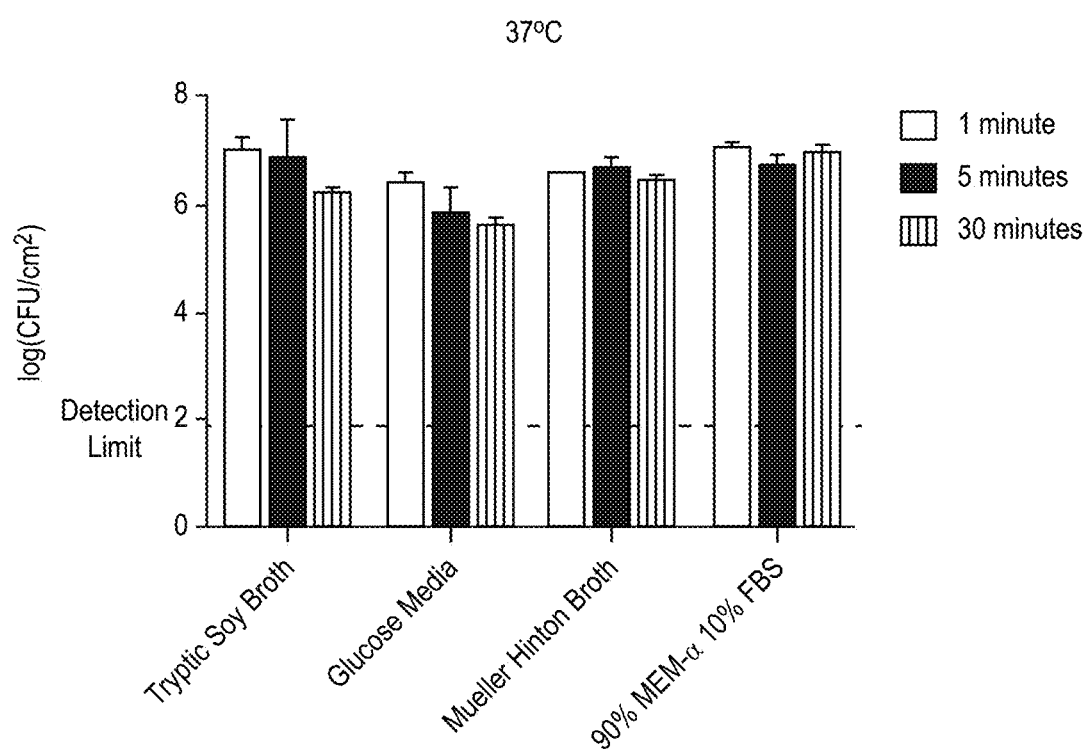
FIG. 18 shows growth media effects data, according to certain embodiments.

Investigating the effect of various growth media, the MHB and MEM-α/FBS produced shaker table biofilms comparable to the shaker table biofilms grown in TBS, as determined by two way ANOVA, with only the GM biofilms differing significantly (p=0.05). These biofilms had a lower bacterial load ($10^{5.94\pm0.49}$ CFU/cm$^2$) than the other control biofilms by over half an order of magnitude, as shown in FIG. 18. This figure also indicates the effect of exposure time. For the control biofilms, the thermal shock temperature was the same as the incubation temperature (37° C.), so the duration of the thermal shock (1 to 30 minutes) was not anticipated to have an effect. This is confirmed by the results in FIG. 17-18, where biofilms from any given medium show no statistical difference (p=0.05) in CFU/cm$^2$ regardless of exposure time to the control temperature. The detection limit indicated in FIG. 18 ($10^{19}$ CFU/cm$^2$) is based on the criterion that plate counts of undiluted biofilm suspension below 3 CFU are not reliably quantified.

Figure 19:
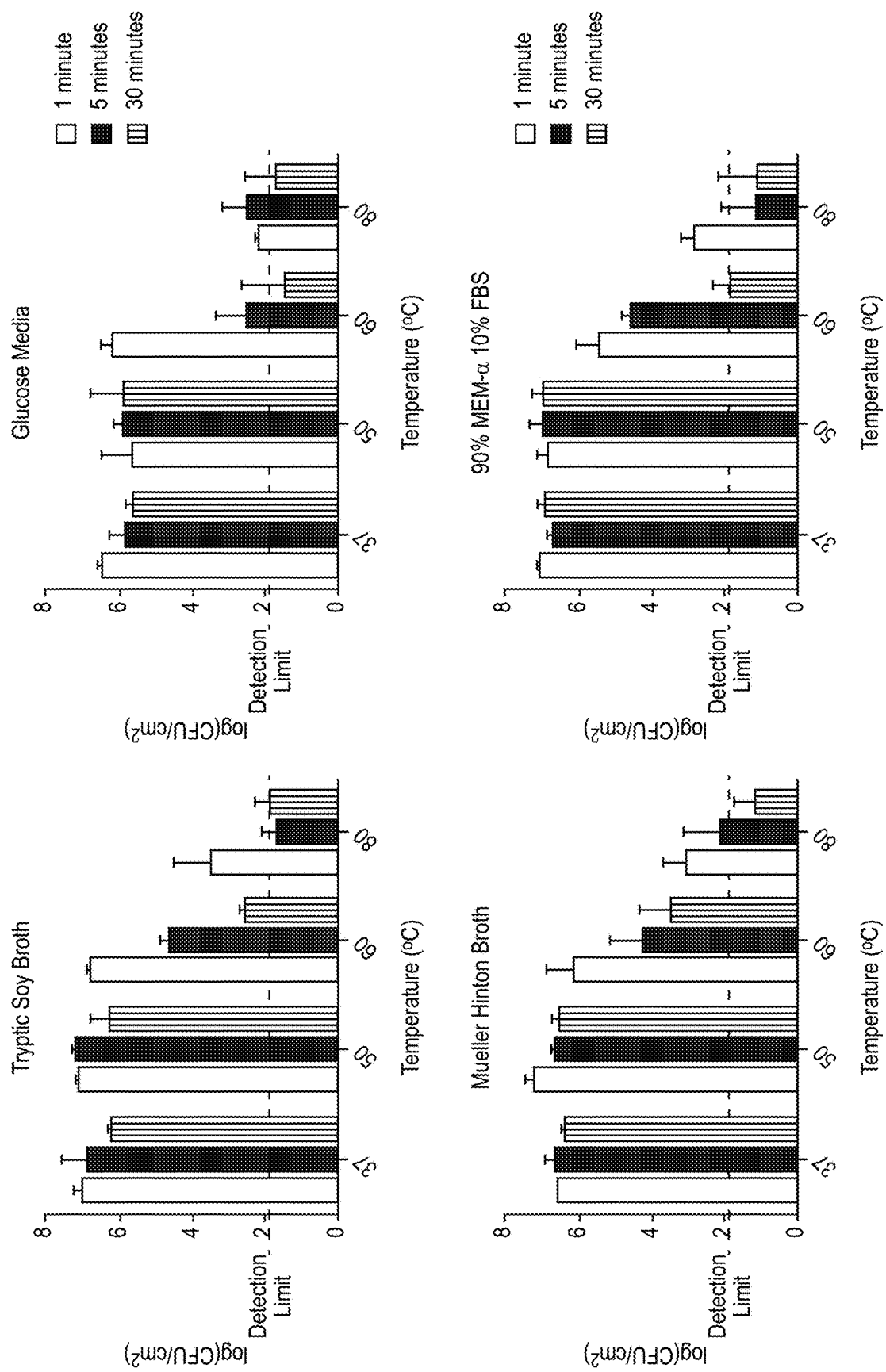
FIG. 19 shows thermal susceptibility and growth media effects data, according to certain embodiments.

Similar observations were made for each of the different growth media types grown on a shaker table. For all media types there was no discernable decrease in bacterial viability after exposure to a 50° C. thermal shock regardless of exposure time. The viable cell count from the biofilms exposed to the 60° C. thermal shock for 1 minute also showed no statistical difference from the controls for all but the biofilms grown in MEM-α/FBS (p=0.05). All biofilms grown on the shaker table showed decreases at 60° C. for exposure times above 1 minute regardless of growth media. Biofilms grown in TSB and GM showed more of a time dependence with the 60° C. thermal shock than others. FIG. 19 summarizes these results for each growth medium, again demonstrating that exposure to 80° C. for more than 1 minute decreased the CFU/cm$^2$ below the quantification limit, sometimes yielding no countable units in the undiluted plated samples.

Example 3: In Situ Mitigation of Bacterial Biofilms Using Magnetic Composite Coatings Iron oxide nanoparticle composites have demonstrated remote heating up to 7.5 W cm$^{-2}$ in both hydrophilic and hydrophobic polymer composites.[4] The use of a magnetic coating to induce thermal shock inside the body will enable a treatment that focuses the energy directly on the implant surface, precisely where the bacteria are growing. The power generated by the composite is a result of the nanoparticle's propensity to convert alternating magnetic field (AMF) energy in to thermal energy.[5] The current investigation is the first to report wireless heating of a P. Aeruginosa biofilms using energy delivered from a polystyrene (PS)/Fe$_3$O$_4$ nanoparticle coating. Microscope slides coated with 226 µm of composite delivered up to 10.9 W cm$^{-2}$ of power when loaded with 30.0% Fe and positioned parallel in a 2.3 kA m$^{-1}$ AMF. The onset of cell death was shown to occur at times and temperatures ranging from 50 to 80° C. for 1 to 30 min with up to 99.9999% reduction in viable biofilm cells occurring at 80° C. exposure for 5 min.

Example 3: Materials and Methods

Iron oxide coating. Fe$_3$O$_4$ nanoparticles were synthesized via a coprecipitation reaction with FeCl$_3$.H$_2$O and FeCl$_2$.4H$_2$O (Sigma Aldrich) in a 2:1 mol ratio under basic conditions (KOH, Sigma Aldrich) using previously published methods.[4, 6] Composite coatings were prepared by dissolving 3.2 g of polystyrene (PS) resin (280,000 MW, Sigma Aldrich) in approximately 40 g of iron oxide nanoparticle slurry (0.082 g g$^{-1}$ Fe in toluene) and cast on frosted glass microscope slides to produce 226±6 µm-thick coatings. After casting, films were dried at ambient conditions for 8 hr followed by 12 hr of drying at 90° C. to evaporate all remaining solvent.

Wireless Heating.

Coatings were remotely heated in a 6-turn AMF generating coil operating at 2.32 kA m$^{-1}$ and 302 kHz with feedback control (operated by an Omega.com iSeries temperature controller) and a fiber optic temperature probe. Coating/microscope slides were positioned parallel to AMF lines in a custom, 3D-printed heating chamber; the temperature probe was positioned directly on the coating's surface. Controller tuning parameters were adjusted to minimize both the time required to reach the specified setpoint and the amount of overshoot from the setpoint.

Example 3: Results

As best shown in FIGS. 20A-22, the presently-disclosed coating and associated systems and methods can successfully disrupt biofilms through the application of a magnetic field.

Figure 20A:
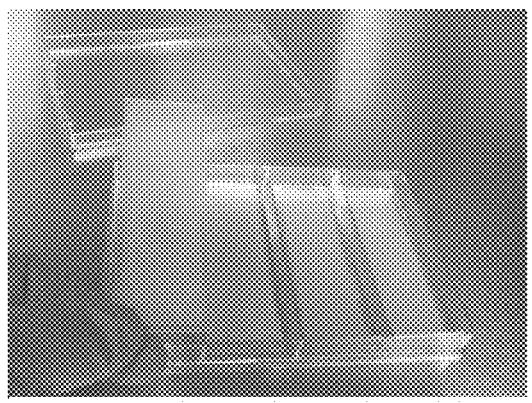
FIG. 20A shows biofilms on glass slides.

FIG. 20A is a picture of biofilms growing on glass microscope slides without coating. In this example, 4-well dishes holding 3"×1" glass microscope slide in each well were treated with 1.39 mL of inoculum in 3.45 mL of glucose media and incubated on an orbital shaker at 130 rpm for 72 hours at 37° C. to grow the biofilm.

Figure 20B:
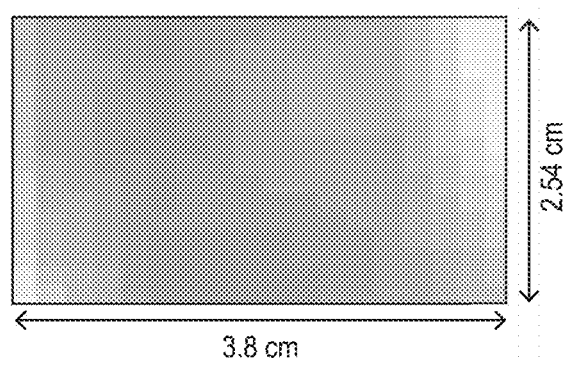
FIG. 20B shows AMF field mapping, according to certain embodiments.

In FIG. 20B depicts AMF field mapping in the same plane as the microscope slide/coating, thereby indicating variation in field strength across entire surface of coating.

Figure 20C:
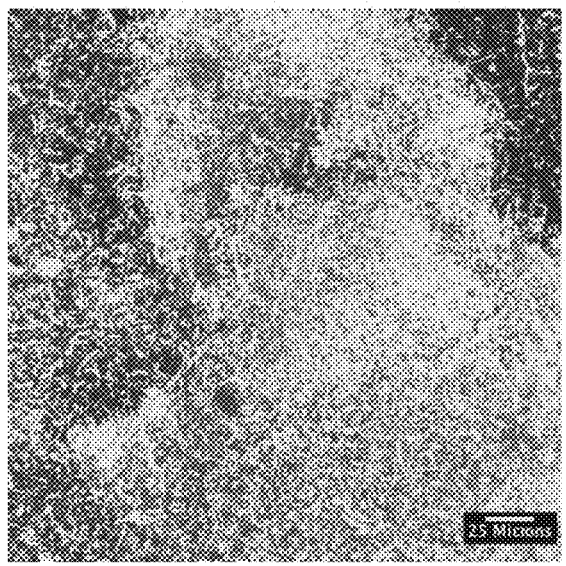
FIGS. 20C-D show composite images of biofilms.
Figure 20D:
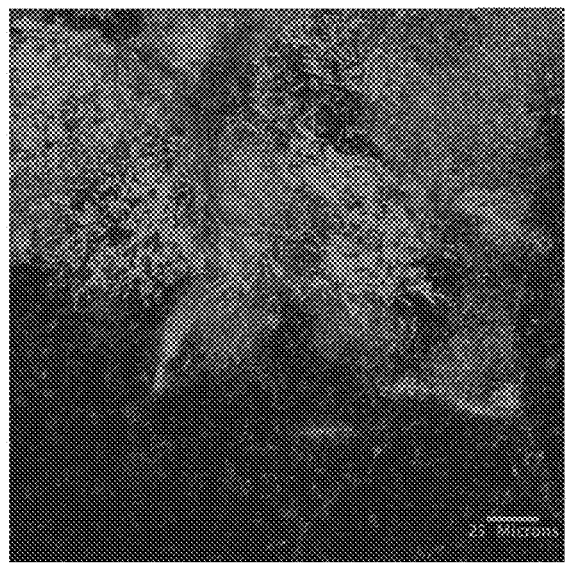

FIGS. 20C-D are composite images of biofilms are stained with Invitrogen's Live/Dead assay and imaged with a confocal fluorescent microscope. These depict biofilms with (FIG. 20D) and without (FIG. 20C) heat treatment. In these images, green cells are alive, red are dead. These biofilms were grown in a drip-flow reactor (as described above) and the heat shock was 30 minutes.

Figure 21:
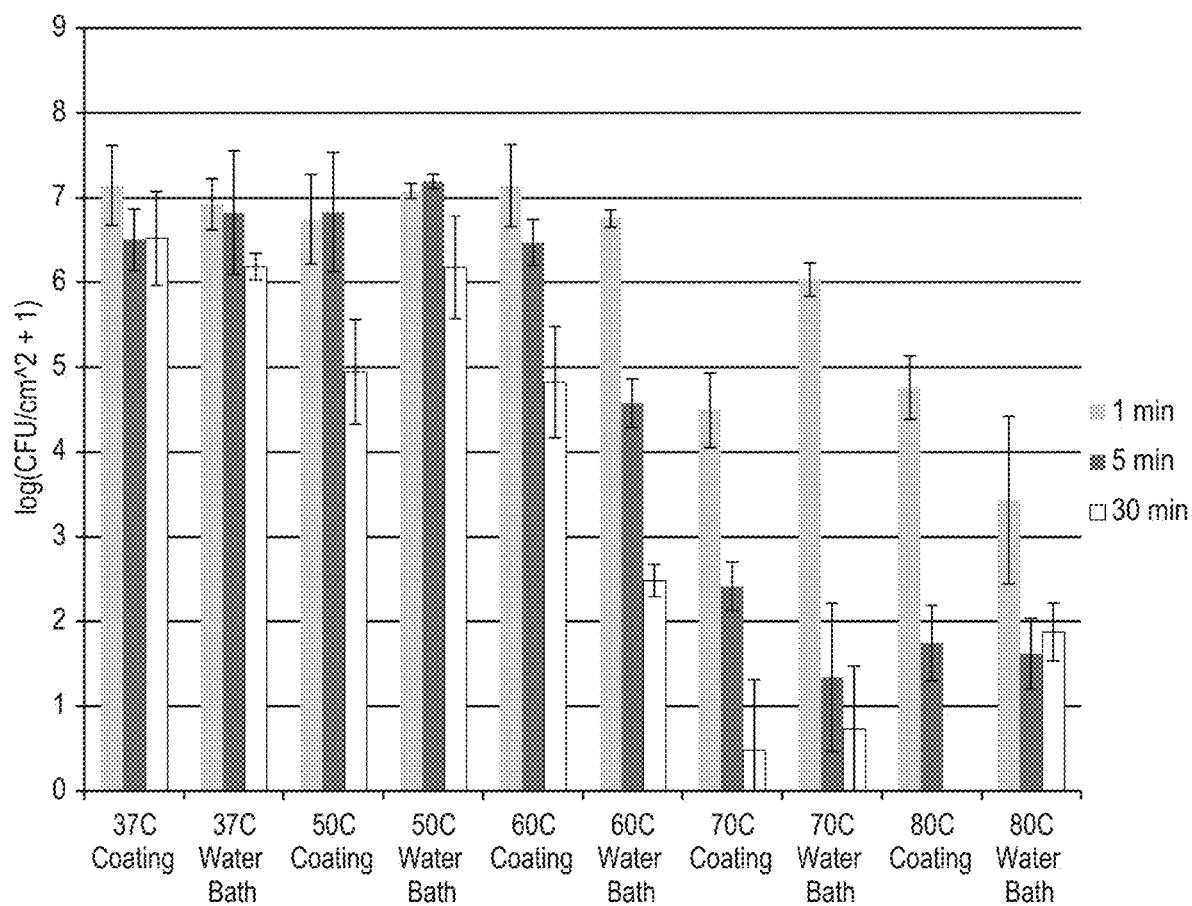
FIG. 21 shows biofilm disruption data, according to certain embodiments.
Figure 22:
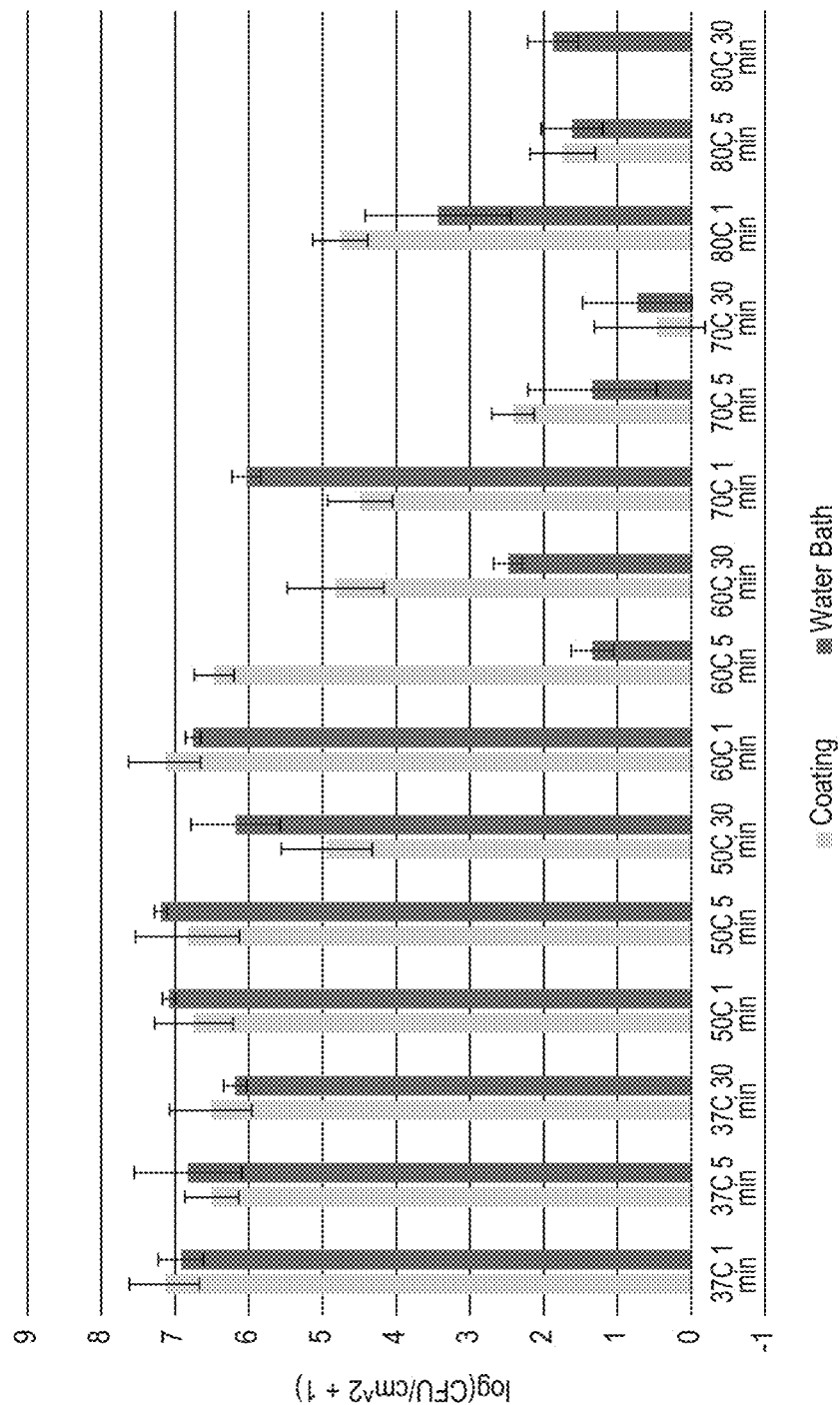
FIG. 22 shows biofilm disruption data, according to certain embodiments.

FIGS. 21-22 depict the results of the water bath heat shock compared to the application of the magnetic field. As is demonstrated, the disruption of biofilm due to application of the magnetic field is in several cases different than that due to water bath heat shock. The disruption of the biofilm due to application of the magnetic field is substantial, such that 80° C. exposure for 30 min via the coating resulted in a 99.9999% reduction in viable biofilm cells. Tables 2-3 depict the underlying results of the water bath and magnetically-induced disruptions.

Although the disclosure has been described with reference to preferred embodiments, persons skilled in the art will recognize that changes may be made in form and detail without departing from the spirit and scope of the disclosed apparatus, systems and methods.

Example 4: Thermal Shock Susceptibility and Regrowth of *Pseudomonas aeruginosa* Biofilms Example 4: Materials and Methods Inoculum

*Pseudomonsa aeruginosa* PAO1 (15692, American Type Culture Collection, Manassas, Va.) stored in glycerol were thawed and streaked onto agar plates (Difco Nutrient Agar, Sparks, Md., USA) and incubated while inverted for 24 hours at 37° C. Two colonies were then removed and placed into 5 mL of sterilized (autoclaved at 121° C. and allowed to cool prior to use) tryptic soy broth (TSB, Becton, Dickinson and Company, Franklin Lakes, N.J., USA) and grown for 24 hours at 37° C., obtaining an average of 2.12× 109±0.07×109 CFU/mL.

Biofilm Growth and Medium Preparation

Glass microscope slides (75 mm×25 mm×1 mm), fully frosted on one side, were placed individually in polystyrene 4-well dishes (Thermo Fisher Scientific, Waltham, Mass., USA) along with 333 µL of the inoculum and 5 mL of media per well, and the dishes were sealed with parafilm. These dishes were placed on an orbital shaker table (VWR 1000, 15 mm orbit, Radnor, Pa., USA) set at 160 rpm in an incubator at 37° C. for 96 hours. Four different media were used: tryptic soy broth, Mueller Hinton broth (MHB, Becton, Dickinson and Company, Franklin Lakes, N.J., USA), a minimum glucose medium (GM), and a mixture containing 90% by volume minimum essential medium a without nucleosides (MEM-α, Thermo Fisher Scientific, Waltham, Mass., USA) mixed with 10% by volume fetal bovine serum (FBS, Thermo Fisher Scientific, Waltham, Mass., USA) to better simulate the growth anticipated in a mammal.

Thirty grams of TSB powder were dissolved into a liter of de-ionized water and heated for 10 minutes in a 700 W microwave. Powder MHB was dissolved at a concentration of 21 g per liter of de-ionized water and similarly heated for 10 minutes in a 700 W microwave. Both TSB and MHB were then autoclaved at 121° C. to ensure sterility. The minimum glucose medium (GM) was made by mixing 1.44 mg ferrous sulfate heptahydrate, 24 mg magnesium sulfate, 2.7 g potassium phosphate dibasic, 2.7042 g glucose, 4.3 g potassium monophosphate, and 5.232 g 3-(N-morpholino) propanesulfonic acid into 500 mL of de-ionized water (all chemical components purchased from Fisher Scientific, Waltham, Mass., USA) and filter sterilized in a 0.2 µm pore nylon vacuum filter (VWR, Radnor, Pa., USA). The 90% MEM-α and 10% FBS (MEM-α/FBS) mixture was made by combining the two components (both liquids) in a 9:1 ratio by volume, MEM-α to FBS, and then filter sterilizing.

Thermal Shock Procedure

After the 96 hour growth period the biofilms and their underlying glass substrates were transferred to a preheated 4-well dish containing 5 mL water per well whose temperature was maintained by a water bath (Isotemp 3013P, Fisher Scientific, Hampton, N.H., USA) at the target temperature. To guard against thermal inertia [45] concerns control trials with thermistor arrays confirmed maintenance of the target temperature in the wells. After the target exposure time the substrate and biofilm were swiftly transferred to the recovery plate, another 4-well dish containing 5 mL water in each well at room temperature. Biofilms were shocked at 50, 60, or 80° C. (plus controls at 37° C.), with exposure times of 1, 5, or 30 minutes. Each condition had at least 12 samples, four parallel replicates of three different plates.

Enumeration

Biofilm population density was quantified via resuspension and plating. After the thermal shock, each 4-well dish of recovered biofilm was wrapped in parafilm and sonicated for 10 minutes at 45 kHz (VWR Symphony, 9.5 L, Radnor, Pa., USA). The homogenized suspension was then serially diluted in tenfold increments and spot plated using 10 μL samples on agar plates (Becton, Dickinson and Company, Franklin Lakes, N.J., USA). After five minutes to let the samples adsorb, the plates were inverted and incubated at 37° C. for 20-24 hours before counting the colony forming units (CFU). The CFUs were then converted into a more relevant logarithmic population density, $$\log\left(\frac{CFU}{cm^2}\right),$$

via Equation 5:

$$\log\left(\frac{CFU}{cm^2}\right) = \log\left[\frac{(\text{plate count}) * 10^{\text{dilution factor}} * \left(\frac{5 \text{ mL}}{0.01 \text{ mL}}\right)}{18.75 \text{ cm}^2}\right] \quad \text{(Equation 5)}$$

where plate count is the number of CFUs in a sample, dilution factor is the number of tenfold dilutions to make that sample, (5 mL/0.01 mL) is the ratio of total biofilm suspension to the volume sampled, and 18.75 cm2 is the surface area of the biofilm's substrate [43]. Plates with counts from 3 CFU to 30 CFU were used for calculations. In the case of two dilution sets landing within this range the lower dilution was used. The upper limit, 30 CFU, was chosen based on the ability to reliably count the individual units without overlap issues and the lower limit, 3 CFU, was established to limit the effect of a single CFU skewing the $$\log\left(\frac{CFU}{cm^2}\right)$$

result by more than log(1.5). In the case when the undiluted sample count was lower than the 3 CFU, the count was used but was below the quantification limit.

Confocal Imaging

Biofilm architecture was observed via confocal fluorescent microscopy. Both enumeration and fluorescent microscopy are destructive techniques, so separate biofilms must be used for each. Bacteria were selectively dyed using a Filmtracer LIVE/DEAD Biofilm Viability Kit (Molecular Probes, Inc., Eugene, Oreg., USA). In this membrane permeability assay Syto9 (excitation wavelength 488 nm, emission wavelength 500 nm, green) enters all cells and fluoresces when bound to nucleic acid, while propidium iodide (excitation wavelength 568 nm, emission wavelength 635 nm, red) can only access cells with damaged membranes, displacing Syto9 in those cells. With non-overlapping emission and excitation peaks, these dyes allow clear differentiation between the dead and live bacteria via confocal microscopy. Thirty microliters each of Syto9 and propidium iodide were added to the recovery well of each biofilm imaged. Biofilms grown in the drip flow reactor (DFR) were imaged using an upright Bio-Rad Radiance 2100 multiphoton/confocal microscope (Hemel-Hempstead, United Kingdom) with a 40× dip lens, while biofilms grown on the shaker table were inspected using a Zeiss LSM 710 confocal microscope (Oberkochen, Germany) with a 63× dip lens. Both microscopes used confocal settings with an argon laser to excite the propidium iodide and a helium-neon laser to excite the Syto9 dye. Biofilms were scanned by horizontal rastering with 1 μm vertical increments from bottom to top. Each row was scanned separately by each laser before advancing to the next row to decrease any overlap in the resulting excitations and emissions. Images were collected in a 1024×1024 pixel array and the resulting images were post-processed in the Java-based ImageJ processor (freely available from the NIH website at http://imagej.nih.gov/ij).

Regrowth Trials

An initial growth curve of the biofilms was determined by enumerating biofilms incubated for 1, 2, 4, 24, or 96 hours, then rinsed for 1 minute in sterile, de-ionized water and resuspended by sonication. Post-shock regrowth was investigated by reincubating thermally shocked biofilms in fresh TSB for 2, 4, 12, 24, or 96 hours, then rinsing for 1 minute in sterile, de-ionized water and resuspending for enumeration. The regrowth of biofilms was investigated after heat shocks at 60° C. for 5, 7.5, and 30 minutes, and 80° C. for 1, 5, and 30 minutes. At least three replicates were performed for each heat shock and regrowth time point.

Statistical Analysis

Statistical analysis of the enumeration results was performed in GraphPad Prism 6. Averages and standard deviations were obtained via arithmetic calculations of log (CFU/cm2) values. A two way ANOVA with a 95% confidence interval set was used to compare the means. The graphs were produced in GraphPad Prism 6 based on the calculated arithmetic mean and standard deviation.

Example 4: Results

Post Thermal Shock Regrowth

Figure 29:
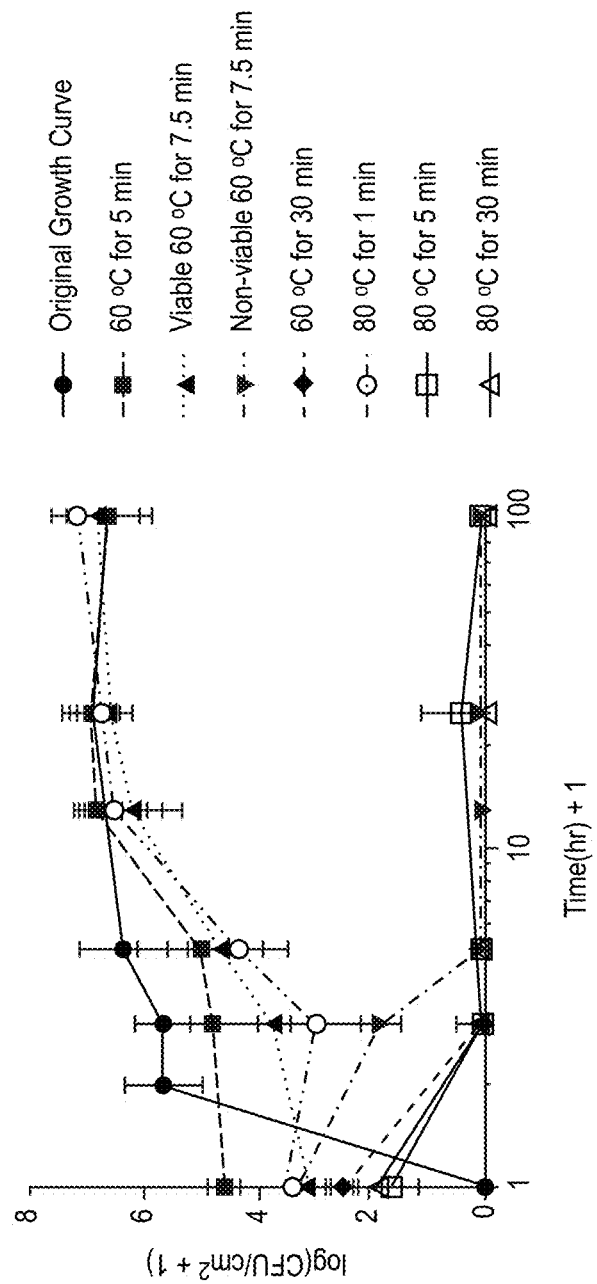
FIG. 29 shows post thermal shock regrowth data, according to certain embodiments.

The original growth curve showed rapid attachment and proliferation within the first hour of inoculation, followed by a prompt climb to a plateau population density averaging 106.64±0.53 CFU/cm2 within four hours, as seen in FIG. 29. By comparison, thermally shocked biofilms showed no growth during their first four hours of reincubation, and required about a half day to reach their pre-thermal shock population density. This plateau density was unaffected by the thermal shock.

Beyond a critical thermal shock intensity, however, the biofilms did not recover. Biofilms shocked at 60° C. for 30 minutes or 80° C. for at least 5 minutes initially showed an average of 102.48 CFU/cm2 and 101.87 CFU/cm2 of surviving bacteria, respectively, but two hours later no CFU were observed in almost all cases. Milder thermal shocks of 60° C. for 5 min or 80° C. for 1 min initially resulted in population densities of 104.58 CFU/cm2, and 103.43 CFU/cm2, respectively, and these biofilms recovered as described above. Biofilms shocked at 60° C. for 7.5 min initially showed 103.1 CFU/cm2; however, upon reincubation, three fourths of the biofilms experiencing this shock subsequently died off, while the remainder recovered as shown in FIG. 29.

Example 5: Synergistic Effects of Heat and Antibiotics on *Pseudomonas aeruginosa* Biofilms Example 5: Material and Methods Biofilm Growth: Cryogenically preserved *Pseudomonas aerugiona* PAO1 (15692, American Type Culture Collection, Manassas, Va.) was thawed and streaked on an agar plate (Difco Nutrient Agar, Sparks, Md., USA). The agar plates were inverted and incubated at 37° C. for 24 hours. An inoculum was made by suspending two colony forming units (CFUs) from the agar plate in five milliliters of sterile tryptic soy broth (TSB, BD Bacto, Sparks, Md., USA) made as directed and incubated at 37° C. for 24 hours, achieving an average concentration of $2.12 \times 10^9 \pm 0.07 \times 10^9$ CFU/mL. One milliliter of inoculum was then diluted into 15 mL TSB and mixed gently. One hundred fifty microliters of the diluted mixture was then placed into each well of the 96-well plate, except for the negative control wells which received 150 μL of TSB. The plate was part of an MBEC™ assay (Innovotech, Edmonton, AB, Canada) in which a corresponding array of 96 pegs protrudes from the plate lid into the wells, providing a convenient array of substrates for biofilm growth which are then readily transferred to new wells (Harrison et al. 2010). The peg lid was placed onto the 96-well plate then sealed using Parafilm and placed on an orbital shaker table (VWR 1000, 15 mm orbit, Thorofare, N.J., USA) at 160 rpm and incubated at 37° C. for 24 hours.

Antibiotic Preparation: A stock of 5 mg/mL ciprofloxacin in sterile, de-ionized water was prepared with ciprofloxacin hydrochloride (MP Biomedicals, Santa Ana, Calif., USA) and mixed thoroughly. Tobramycin stock was made in a similar fashion by mixing 5 mg/mL tobramycin sulfate salt (Sigma-Aldrich, St. Louis, Mo., USA) in sterile, de-ionized water. Erythromycin was obtained from MP Biomedicals and the stock was prepared by mixing 5 mg/mL erythromycin into ethanol. Each antibiotic mixture was then filter sterilized through a 0.22 μL PES membrane sterile filter (Millex®GP filter unit) and stored at 2° C. Each antibiotic was then diluted from the stock solution into sterile TSB at an array of concentrations in a 96-well challenge plate used that day.

Antibiotic Exposure: After 24 hr of growth, the array of biofilm-covered pegs was transferred into a 96-well rinse plate (Costar® 96 well flat bottom cell culture, Corning Incorporated, NY, USA) containing 200 μL/well de-ionized, sterile water at ambient temperature for 2 min to remove bacteria not incorporated in the biofilm. The peg lid was then transferred to a 96-well challenge plate of wells containing 200 μL of various concentrations of ciprofloxacin, tobramycin, or erythromycin diluted in TSB. For the antibiotic experiments without thermal shock the peg lid was exposed to a single challenge plate for 24 hours in an incubator at 37° C. before rinsing again for 2 min in a new rinse plate. The peg lid was then transferred to a recovery plate containing 200 μL/well fresh, sterile TSB for resuspension and enumeration.

Antibiotic and Thermal Exposure: To investigate the combined effect of antibiotics and thermal shock, biofilms cultured and exposed to antibiotics as discussed above were removed from their antibiotic challenge plate after only four hours. They were quickly transferred to a challenge plate with the same array of antibiotic concentrations, preheated to the target temperature by a thermostatted water bath. Temperatures of 37° C., 50° C., 60° C., 70° C., and 80° C. were studied at exposure times of 1, 5, and 30 min. The pegs were left in the heated challenge plate for the desired exposure time, then transferred to a new challenge plate with the same antibiotic concentrations at 37° C. and incubated for the remainder of the total 24 hour antibiotic exposure time. Following 24 total hours of antibiotic exposure time the peg lid was rinsed once again for two minutes in a new rinse plate and placed into a recovery plate for resuspension and enumeration. Each growth and challenge plate step is shown in FIG. 1.

Biofilm Enumeration: To disrupt the biofilm and resuspend the bacteria in a homogenous solution for serial dilution, each recovery plate with biofilm covered pegs was sonicated for ten minutes at 45 kHz in a VWR Symphony 9.5 L sonicator (Radnor, Pa., USA). The sonicated recovery plates were serially diluted tenfold in a 96-well flat bottom culture plate. Twenty microliters of each dilution were spot plated on agar plates and allowed to absorb for approximately 20 minutes before the agar plates were inverted and incubated at 37° C. for 20 to 24 hours. The resulting colony forming units (CFUs) were then counted and recorded. The logarithmic population density $$\log\left(\frac{CFU}{peg}\right),$$

was calculated using Equation 6:

$$\log\left(\frac{CFU}{peg}\right) = \log\left[\frac{(\text{plate count}) * 10^{\text{dilution factor}} * \left(\frac{200\ \mu L}{20\ \mu L}\right)}{peg} + 1\right] \quad \text{(Equation 6)}$$

where the dilution factor is the number of tenfold dilutions corresponding to the sample counted and the plate count is the number of CFUs counted in that sample. The (200 μL/20 μL) is the ratio of the total recovery suspension to the amount that was sampled. Dilutions showing 3 to 50 CFUs were used for analysis; when two dilutions fit this range, the less dilute sample was used. The upper bound (50) prevents counting error due to overlapping CFUs and the lower bound (3) prevents a single CFU from altering the $$\log\left(\frac{CFU}{peg}\right)$$

value by more than 0.125 by chance. By this rubric, population densities below $$\log\left(\frac{CFU}{peg}\right) = 1.49$$

cannot be quantified. In cases where the undiluted recovery well sample yielded less than 3 CFUs, lower $$\log\left(\frac{CFU}{peg}\right)$$

were calculated but should be considered below the quantification limit. For samples with no CFU evident, the "+1" in Equation 6 ensured that the $$\log\left(\frac{CFU}{peg}\right)$$

value was U rather than mathematically undefined; its effect on values above the quantification limit is negligible.

Optical Density Measurements of Planktonic Bacteria: The planktonic bacteria that had escaped the biofilm via dispersion after the thermal treatment were optically observed to better understand the biofilm's dispersion post-thermal treatment while antibiotics were still present. To estimate the free-swimming bacteria following the antibiotic treatment, the optical density (BioTek Gen5 Microplate Reader, Winooski, Vt., USA) at 600 nm was measured for each well in the second challenge plate. The negative controls in the challenge plate contained only TSB and were used to calculate an average background.

Statistical Analysis: The statistical analysis of both the planktonic optical density reads and the logarithmic CFU counts were reported via their arithmetic mean and standard deviation. The reported optical density numbers had a measured average background of 0.8 subtracted from their original raw values. Statistical analysis was performed in GraphPad Prism 7 using the two-way ANOVA with a confidence interval of 95%.

Example 5: Results

Figure 23:
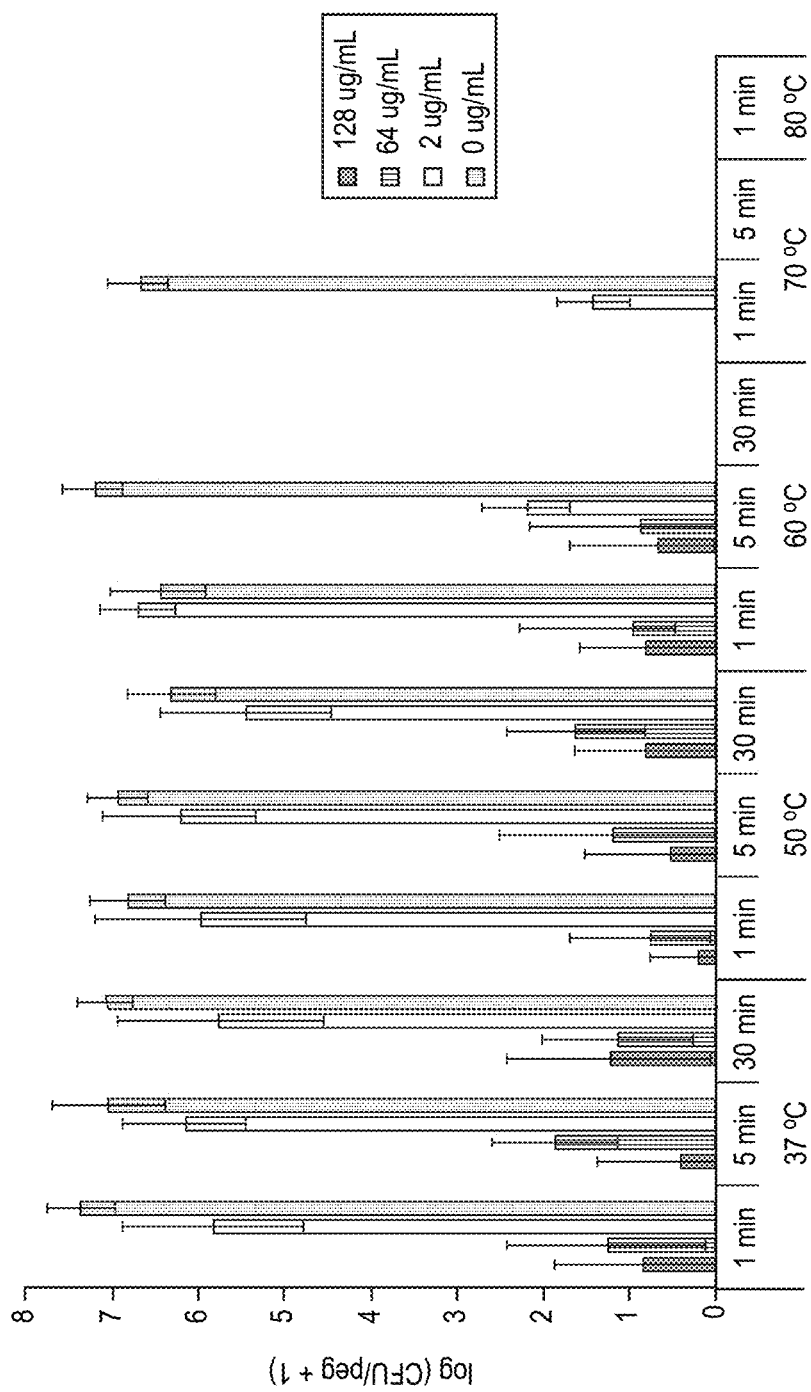
FIG. 23 shows data on the effect of ciprofloxacin and heat on biofilms, according to certain embodiments.
Figure 24:
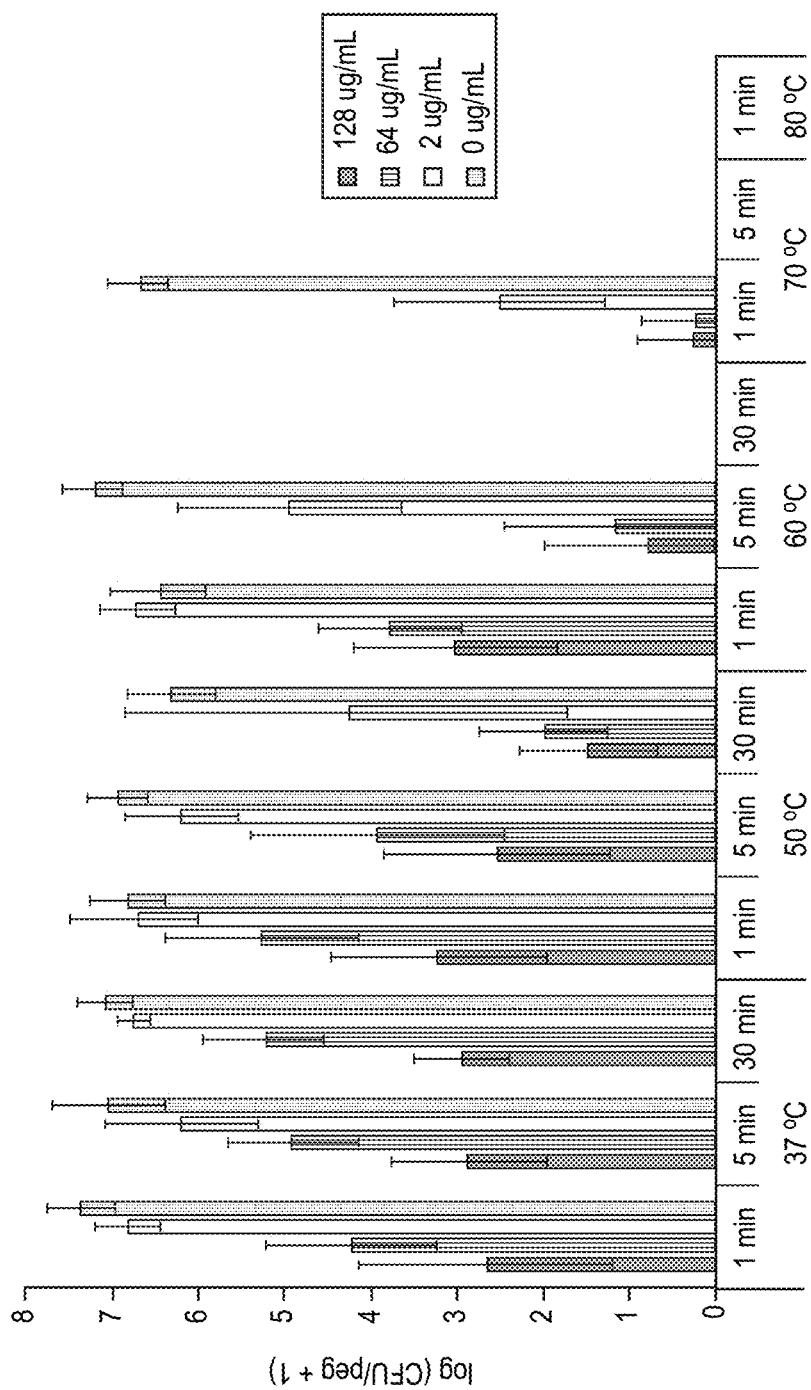
FIG. 24 shows data on the effect of tobramycin and heat on biofilms, according to certain embodiments.
Figure 25:
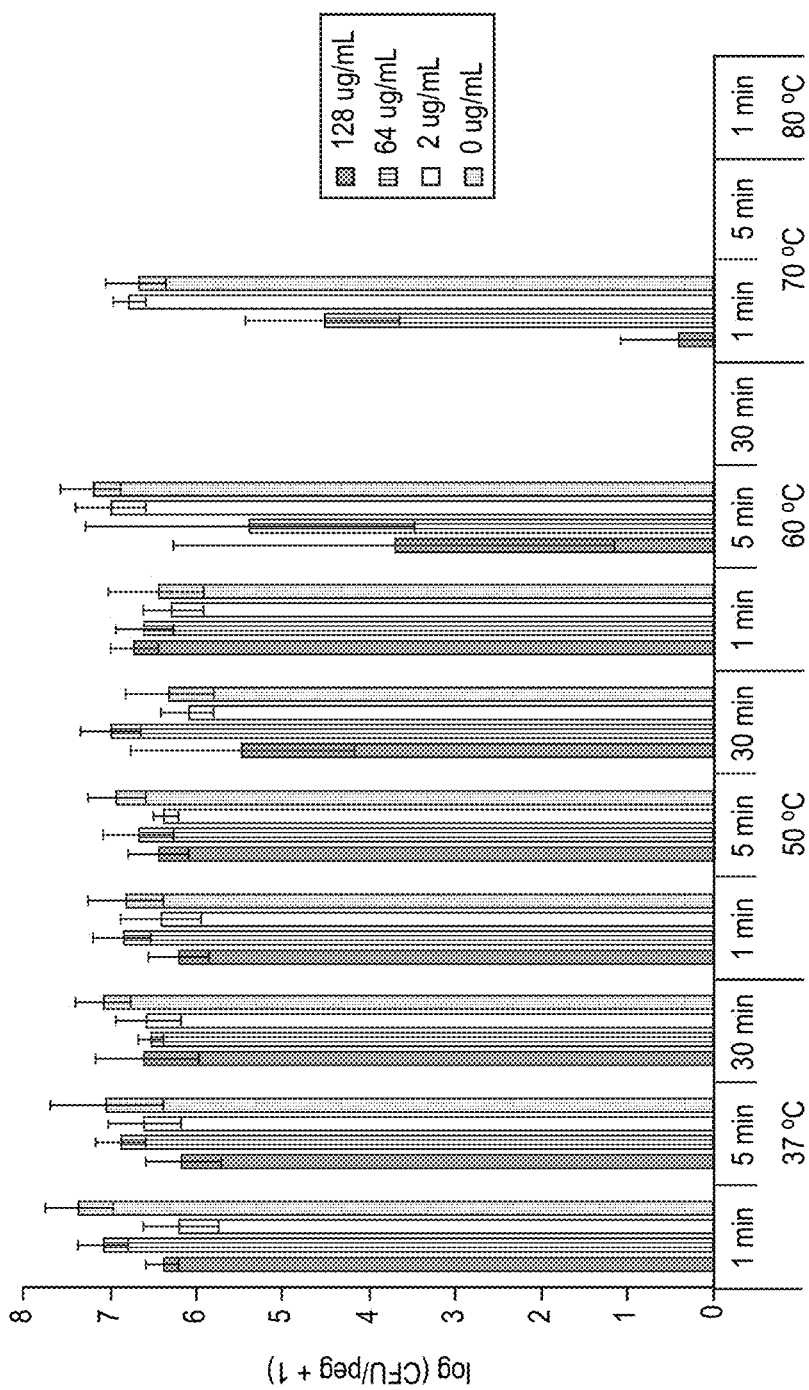
FIG. 25 shows data on the effect of erythromycin and heat on biofilms, according to certain embodiments.

Effect of Antibiotics and Heat on Biofilms: The biofilms were more resistant to both heat and antibiotics than their planktonic counterparts. Without antibiotics, the thermal treatment alone resulted in a binary effect, killing all the biofilm bacteria at 60° C. for 30 min, 70° C. for 5 min, and 80° C. for 1 min, while milder treatments had no statistically significant effect, as seen in FIGS. 23 through 25. Without thermal shock, the biofilms to fresh 37° C. wells had little impact on biofilm viability. These results reconfirm that while ciprofloxacin and tobramycin at higher concentrations significantly reduce biofilm populations, they cannot, on their own, reliably eliminate them as seen with the more aggressive thermal shocks. Even at low concentrations, however, those antibiotics have a significant synergistic impact within a key window of thermal shock conditions.

Ciprofloxacin at the bloodstream concentration, 4 µg/mL, and at 1 µg/mL substantially reduced biofilms with at least a five-order magnitude decrease in viable bacteria regardless of the heating, seen in FIG. 23. Combined with 70° C., 1 min thermal shocks, these ciprofloxacin concentrations left no viable bacteria, however, despite the fact that the 70° C. 1 min thermal shock by itself had no discernible effect. Even the 0.125 µg/mL ciprofloxacin concentration, which had little effect on biofilms by itself, reduced biofilm populations by five orders of magnitude when combined with otherwise ineffective thermal shocks at 60° C. for 5 min and 70° C. for 1 min.

Tobramycin was the second most effective antibiotic on its own and demonstrated this synergy with heat more clearly than either of the other two antibiotics. FIG. 24 shows the trend of prolonged thermal exposure time increasing the overall efficacy of biofilm mitigation at all non-zero tobramycin concentrations, regardless of temperature. No trend is seen at the control temperature (37° C.) nor is this trend observed without tobramycin, except for complete elimination at 60° C. for 30 min, 70° C. for 5 min, and 80° C. for 1 min as mentioned earlier. Within each of the concentration sets for tobramycin the 50° C. for 30 min and the 60° C. for 5 min exposures resulted in similar mitigation amounts. At 50° C. for 30 min, 60° C. for 5 min, and 70° C. for 1 min the effect of the combined thermal shock and antibiotics was larger than either treatment by itself.

Erythromycin showed no effect at any concentration for the control temperature, 37° C., nor in combination with 50° C. thermal treatments as seen in FIG. 25. However, biofilms heated at 60° C. for 5 min and treated with 64 µg/mL or 128 µg/mL erythromycin decreased in viable bacteria by an average of 1.5 log(CFU/peg) and 2.7 log(CFU/peg), respectively. At 70° C. for 1 min the biofilms exposed to 64 µg/mL decreased by 2.3 log(CFU/peg) and when exposed to 128 µg/mL the number of viable bacteria decreased by 6.0 log(CFU/peg). Similar to the other antibiotics, the combined antibiotics and thermal shock approach showed the greatest increase in efficacy over either individual treatment in the thermal shock window of 60° C. for 5 min to 70° C. for 1 min.

Figure 26:
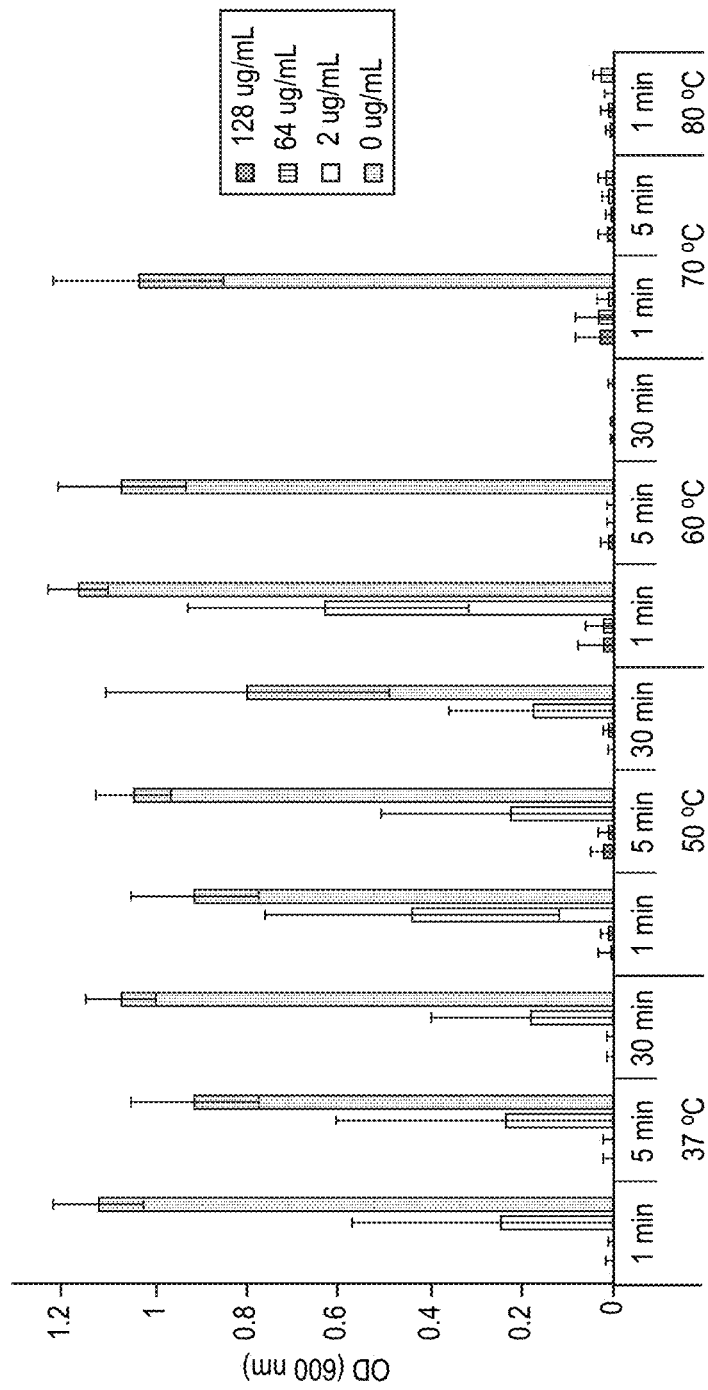
FIG. 26 shows data on the effect of ciprofloxacin and heat on dispersed planktonic bacteria, according to certain embodiments.
Figure 27:
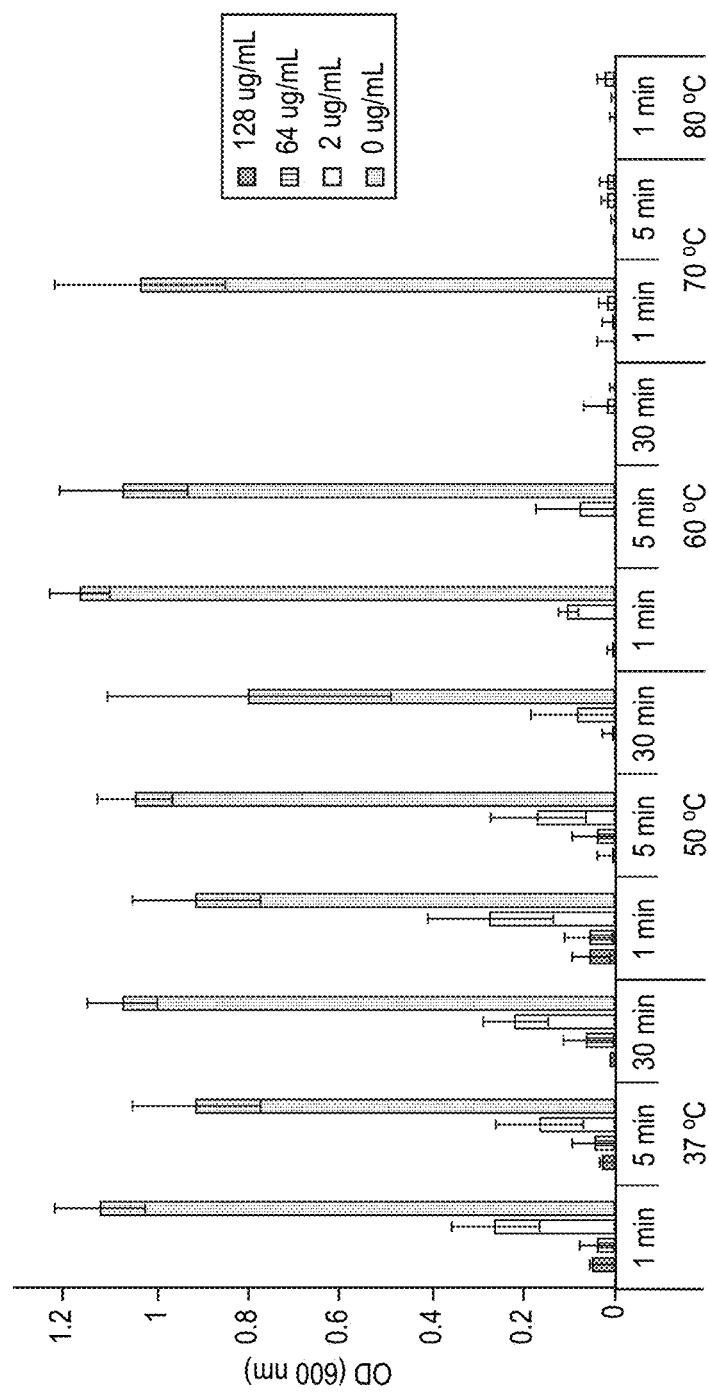
FIG. 27 shows data on the effect of tobramycin and heat on dispersed planktonic bacteria, according to certain embodiments.
Figure 28:
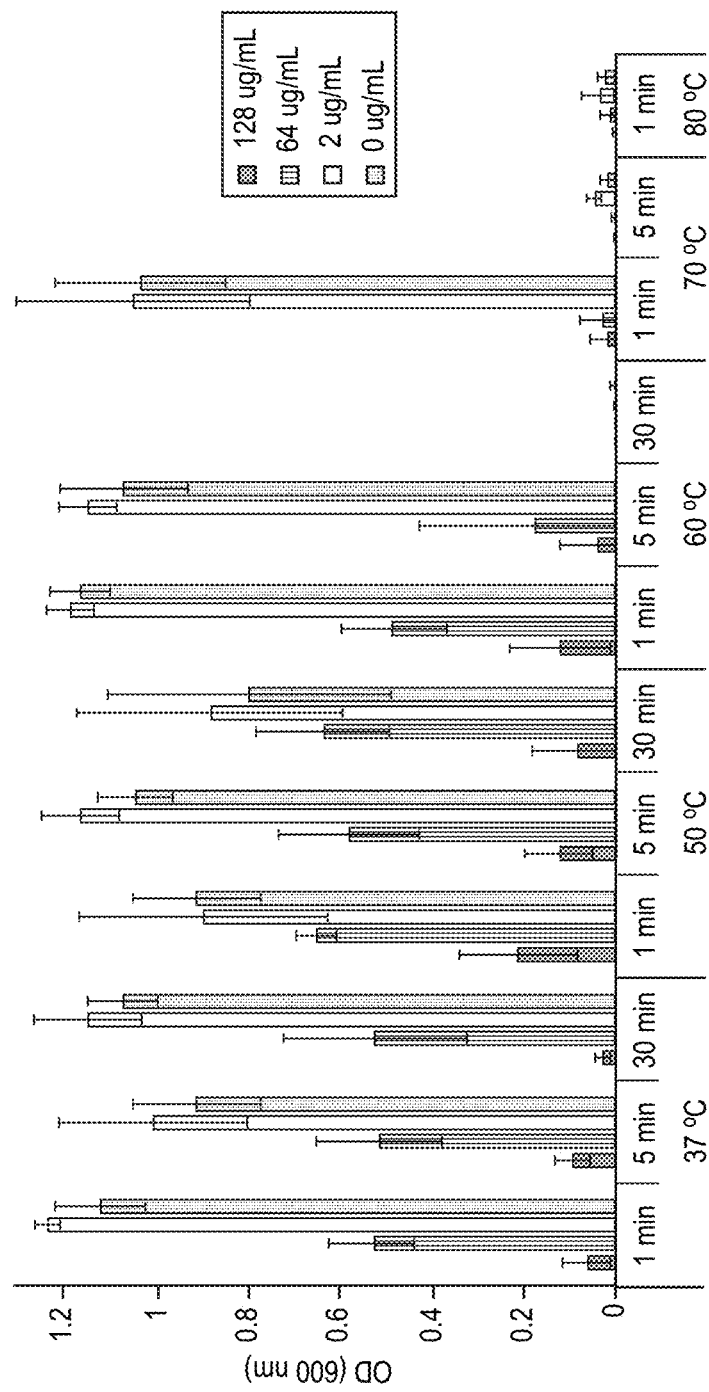
FIG. 28 shows data on the effect of erythromycin and heat on dispersed planktonic bacteria, according to certain embodiments.

Effect of Antibiotics and Heat on Dispersed Planktonic Bacteria: Further confirming the biofilm measurements, the media in which the biofilms incubated after thermal shock showed virtually no bacteria for treatments in which the corresponding biofilm was destroyed. Moreover, in antibiotic free trials the thermal shock had no apparent effect on the bacteria's ability to disperse from the biofilm and repopulate a fresh well. However, the presence of antibiotics strongly inhibited planktonic bacterial growth regardless of the presence of thermal shock. All three concentrations of ciprofloxacin, 0.125, 1.0, and 4.0 µg/mL seen in FIG. 26, and tobramycin, 1.0, 2.0, and 4.0 µg/mL seen in FIG. 27, were effective against the planktonic bacteria with the higher two of the three concentrations killing off almost all the free-swimming bacteria regardless of thermal shock. Erythromycin had no discernible effect at 2 µg/mL as seen in FIG. 28. However, at 64 µg/mL there appeared to be a significant reduction in population even without thermal shock, and a further decrease in viable planktonic bacterial cells at 128 µg/mL. Notably, while a 60° C. thermal shock for 5 min had no effect by itself, in the presence of erythromycin the bacteria population was significantly reduced from the non-thermal-shocked values, this effect was even more pronounced with a thermal shock at 70° C. for 1 min. The synergistic effect of antibiotics with thermal shocks at 60° C. for 5 min and 70° C. for 1 min were observed with all the antibiotics, but most prominent with erythromycin.

What is claimed is:

1. A system for disrupting a biofilm on a medical device, comprising:
   a. an implantable medical device;
   b. a magnetically-sensitive coating on the surface of the implantable device comprising:
      i. magnetic particles, and
      ii. a polymer,
      wherein the magnetically-sensitive coating is capable of converting energy from an alternating magnetic field into thermal energy sufficient to disrupt the biofilm on the medical device; and
   c. a coil element capable of generating an alternating magnetic field,
   wherein the coil element is constructed and arranged to apply an alternating magnetic field to heat the surface of the implantable device to at least about 50° C., and wherein the surface of the device has a plurality of zones and wherein each zone of the plurality of zones has distinct areal concentration of magnetic susceptibility,
   wherein the areal concentration of magnetic susceptibility in zones perpendicular to the applied magnetic field lines is twice as large as the areal concentration of magnetic susceptibility in zones parallel to the applied magnetic field lines.

2. The system of claim 1 wherein, upon implantation of the device into the body of a subject, the areal concentration of magnetic susceptibility in each zone is proportional to its heat transfer coefficient to the body tissue in contact with that zone.

3. The system of claim 1 wherein the areal concentration of magnetic susceptibility in each zone is scaled by both its heat transfer coefficient to the body tissue in contact with that zone and its orientation to the applied magnetic field lines.

4. The system of claim 1, wherein the plurality of zones comprises a first zone and a second zone and wherein the areal concentration of magnetic susceptibility in the first zone is about twice the areal concentration of magnetic susceptibility in the second zone and wherein the alternating magnetic field comprises a magnetic axis that is perpendicular to the first zone and parallel to the second zone and wherein application of the alternating magnetic field to the implantable device generates equal increases in temperature in the first zone and the second zone.

5. The system of claim 1, wherein the implantable medical device comprises a temperature sensor constructed and arranged to detect temperature changes on the surface of the implantable device.

6. The system of claim 5, comprising a coil element controller, configured to receive temperature information from the temperature sensor and further configured to deliver an alternating magnetic field until the surface of the implantable device reaches a predetermined temperature threshold.

7. The system of claim 1 wherein the alternating magnetic field is discontinued when the surface of the implantable device reaches at least about 50° C. for a predetermined interval of time and wherein the predetermined time interval is between about thirty seconds and thirty minutes.

8. A system for disrupting a biofilm on a medical device, comprising:
   a. an implantable medical device;
   b. a magnetically-sensitive coating on the surface of the implantable device comprising:
      i. magnetic particles, and
      ii. a polymer,
      wherein the magnetically-sensitive coating is capable of converting energy from an alternating magnetic field into thermal energy sufficient to disrupt the biofilm on the medical device; and
   c. a coil element capable of generating an alternating magnetic field,
   wherein the coil element is constructed and arranged to apply an alternating magnetic field to heat the surface of the implantable device to at least about 50° C., and wherein the surface of the device has a plurality of zones and wherein each zone of the plurality of zones has distinct areal concentration of magnetic susceptibility,
   wherein the plurality of zones comprises a first zone and a second zone and wherein the areal concentration of magnetic susceptibility in the first zone is about twice the areal concentration of magnetic susceptibility in the second zone and wherein the alternating magnetic field comprises a magnetic axis that is perpendicular to the first zone and parallel to the second zone and wherein application of the alternating magnetic field to the implantable device generates equal increases in temperature in the first zone and the second zone.

\* \* \* \* \*